(12) United States Patent
Shen et al.

(10) Patent No.: US 12,168,659 B2
(45) Date of Patent: Dec. 17, 2024

(54) THIOAMIDE DERIVATIVE AND PREPARATION METHOD AND APPLICATION THEREOF

(71) Applicant: Yunbaiyao Zhengwu Science and Technology (Shanghai) Co., Ltd., Shanghai (CN)

(72) Inventors: Zhengwu Shen, Shanghai (CN); Bin Deng, Kunming (CN); Mengqi Zhang, Kunming (CN); Hongzhu Bian, Shanghai (CN)

(73) Assignee: Yunbaiyao Zhengwu Science and Technology (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 18/646,687

(22) Filed: Apr. 25, 2024

(65) Prior Publication Data
US 2024/0327405 A1    Oct. 3, 2024

Related U.S. Application Data

(63) Continuation of application No. PCT/CN2022/105721, filed on Jul. 14, 2022.

(30) Foreign Application Priority Data

May 23, 2022   (CN) .................. 202210564915.X

(51) Int. Cl.
*C07D 471/04*   (2006.01)
*A61K 31/519*   (2006.01)
(Continued)

(52) U.S. Cl.
CPC .......... *C07D 471/04* (2013.01); *A61K 31/519* (2013.01); *A61K 45/06* (2013.01); *A61P 35/00* (2018.01)

(58) Field of Classification Search
CPC ..... C07D 471/04; A61P 35/00; A61K 31/519; A61K 45/06
See application file for complete search history.

(56) References Cited

U.S. PATENT DOCUMENTS 8,835,443 B2 * 9/2014 Kawasaki ............... A61P 29/00
514/262.1

FOREIGN PATENT DOCUMENTS

| CN | 101912400 A | 12/2010 |
| CN | 110012668 A | 7/2019 |

(Continued)

OTHER PUBLICATIONS

Schafer et al. Drug Discovery Today 2008, 13 (21/22), 913-916 (Year: 2008).*

(Continued)

*Primary Examiner* — Daniel R Carcanague
*Assistant Examiner* — Jerica Katlynn Wilson

(57) ABSTRACT

A thioamide derivative of formula (I) and a preparation method thereof:

(Continued)

An application of the thioamide derivative, or an isomer, a pharmaceutically-acceptable salt, or a prodrug molecule thereof in the preparation of a drug for the treatment of cancer is also provided. The thioamide derivative is a new compound with high antitumor activity, and can be used for antitumor therapy alone or in combination with other drugs.

7 Claims, 2 Drawing Sheets

(51) Int. Cl.
*A61K 45/06* (2006.01)
*A61P 35/00* (2006.01)

(56) References Cited

FOREIGN PATENT DOCUMENTS

| | | | |
|---|---|---|---|
| CN | 112261970 | A | 1/2021 |
| CN | 112334194 | A | 2/2021 |
| CN | 113754680 | A | 12/2021 |
| CN | 114853754 | A | 8/2022 |
| TW | 201706256 | A | 2/2017 |
| TW | 202144347 | A | 12/2021 |
| WO | 2005121142 | A1 | 12/2005 |
| WO | 2021263188 | A1 | 12/2021 |

OTHER PUBLICATIONS

Horig et al. Journal of Translational Medicine 2004, 2(44) (Year: 2004).*

Hofner et al. J Adv Pract Oncol. 2018; 9(7): 741-745 (Year: 2018).*
https://us.tafinlarmekinist.com/ (Year: 2024).*
Kumari et al. (J. Med. Chem. 2020, 63, 21, 12290-12358 (Year: 2020).*
p. 21; https://www.accessdata.fda.gov/drugsatfda_docs/label/2018/204114s007lbl.pdf). (Year: 2018).*
Zheng Wei Lee et al., "The slow-releasing hydrogen sulfide donor, GYY4137, exhibits novel anti-cancer effects in vitro and in vivo", PLoS one, Jun. 2011, vol. 6, Issue 6, e21077, Entire document.
Khosrow Kashfi, "Anti-cancer activity of new designer hydrogen sulfide-donating hybrids", Antioxidants & Redox Signaling, Feb. 10, 2014, vol. 20, No. 5, pp. 831-846.
Csaba Szabo, "Gasotransmitters in cancer: from pathophysiology to experimental therapy", Nature Reviews Drug Discovery, Mar. 2016, vol. 15, No. 3, pp. 185-203.
Fangfang Cai et al., "ADT-OH, a hydrogen sulfide-releasing donor, induces apoptosis and inhibits the development of melanoma in vivo by upregulating FADD", Cell Death and Disease, Jan. 16, 2020, 11(1):33, Entire document.
Z-W Lee et al., "Utilizing hydrogen sulfide as a novel anti-cancer agent by targeting cancer glycolysis and pH imbalance." British Journal of Pharmacology, 2014, vol. 171, No. 18, pp. 4322-4336.
Jinfang Jiang et al., "Role of human liver and intestine esterases in drug design and development", Acta Pharmaceutica Sinica, 2018, vol. 53, No. 2, pp. 177-185.
Xu Cao et al., "A Review of Hydrogen Sulfide Synthesis, Metabolism, and Measurement: Is Modulation of Hydrogen Sulfide a Novel Therapeutic for Cancer?", Antioxidants & Redox Signaling, 2019, vol. 31, No. 1, pp. 1-38.

* cited by examiner

THIOAMIDE DERIVATIVE AND PREPARATION METHOD AND APPLICATION THEREOF

CROSS-REFERENCE TO RELATED APPLICATIONS

This application is a continuation of International Patent Application No. PCT/CN2022/105721, filed on Jul. 14, 2022, which claims the benefit of priority from Chinese Patent Application No. 202210564915.X, filed on May 23, 2022. The content of the aforementioned application, including any intervening amendments thereto, is incorporated herein by reference in its entirety.

TECHNICAL FIELD

This application relates to pharmaceutical chemistry, and more particularly to a thioamide derivative, and a preparation method and application thereof.

BACKGROUND

Upregulation of mitogen-activated protein kinase (MAPK) expression is often a hallmark of oncogenic transformation and cancer development. The MAPK pathway can transmit signals from extracellular receptors to intracellular receptors. The Raf-MEK-ERK pathway (Raf: rapidly accelerated fibrosarcoma; MEK: mitogen-activated extracellular signal-regulated kinase; ERK: extracellular signal-regulated kinase) is one of the most well-defined signaling cascades within the MAPK pathway, and its activation plays an important role in the proliferation, differentiation, invasion, and metastasis of cancer cells. As a consequence, it has become an important target for research and development of anti-cancer drugs.

Currently, three subtypes of Raf have been identified: A-Raf, B-Raf, and C-Raf. These three Raf family members can phosphorylate MAPK/ERK kinases (MEK), among which B-Raf may be the most dangerous catalyst for melanoma. MEK 1/2 dual-specificity protein kinase is the only known B-Raf enzyme substrate. MEK mutations are rare in cancer, but MEK activity reveals the danger of B-Raf signaling mutations.

In cells, various cell signalling molecules bind to tyrosine receptors, control the activation of the proto-oncogene product RAS, and then phosphorylate Raf, activating MEK (MEK1 and MEK2) and its unique substrate ERK (ERK1 and ERK2) in a cascade signalling manner. The action of ERK on various downstream substrates regulates a number of key cellular activities, including cell proliferation, invasion, angiogenesis and resistance to apoptosis. Approximately one third of human cancers are closely associated with RAS mutations.

B-Raf mutations are present in most malignant melanomas and papillary thyroid carcinomas. More than 90% of these mutations involve an adenine to thymine substitution at position 1796 of the B-Raf gene (T1796A), resulting in a valine to glutamic acid mutation at position 600 of the B-Raf protein (V600E), and the mutant B-Raf can directly activate MEK. MEK inhibitors have significant therapeutic effects on malignancies caused by B-Raf mutations, particularly in cancer cell lines with B-Raf mutations (V600E) where the negative feedback mechanism of the MEK pathway is absent, making such cancer cells much more sensitive to MEK inhibitors.

Drug resistance to MEK inhibitors is inevitable in the treatment of cancer. Resistance to MEK inhibitors can be divided into innate resistance and acquired resistance. Innate resistance refers to the complete ineffectiveness of MEK inhibitors. However, in most patients, MEK inhibitor therapy is usually effective at the outset, and disease relapse due to loss of drug efficacy can be considered acquired resistance. Acquired resistance severely limits the efficacy of MEK inhibitors. In preclinical studies, the combination of different inhibitors such as mammalian target of rapamycin (mTOR), phosphoinositide 3-kinase (PI3K), serine/threonine protein kinase (AKT), Raf, etc. has been investigated and it has been shown that the combination of dual pathway inhibitors of the ERK/MAPK cascade and the PI3K/AKT pathway is effective and has been used in clinical treatment. In addition to inhibiting the ERK/MAPK pathway, MEK inhibitors can also upregulate a variety of other kinases, such as dual-specificity tyrosine phosphorylation-regulated kinase (Dyrk1B). Therefore, the development of inhibitors for such kinases is also a potential solution to the problem of MEK inhibitor resistance.

Trametinib is a MEK inhibitor being developed by GlaxoSmithKline (GSK) plc. for the treatment of melanoma. It was approved by the FDA in 2013 and is marketed under the brand name MEKINIST. MEKINIST is a single oral tablet for the treatment of unresectable or metastatic melanoma in adult patients harbouring the B-Raf V600E or V600K mutation. In 2014, the FDA approved Trametinib in combination with the BRAF inhibitor Dabrafenib for the treatment of unresectable or metastatic melanoma with the B-Raf V600E or V600K mutation. In 2017, the FDA approved the combination of Dabrafenib and Trametinib for the treatment of non-small cell lung cancer patients with the B-Raf V600E mutation, with an efficacy rate of over 60%.

Trametinib has the following structure:

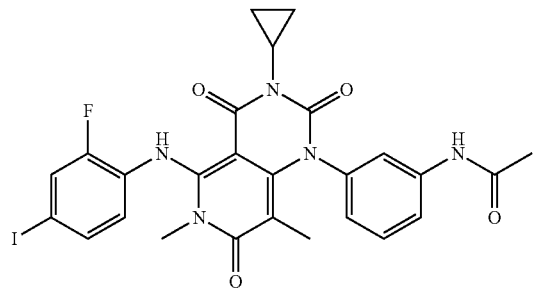

Arylacetamide deacetylase (AADAC) is a microsomal serine esterase with a relative molecular weight of 45 kDa. It is expressed primarily in the liver, intestine and bladder. AADAC can promote the hydrolysis of amide derivatives in vivo. In addition, various cholinesterases exist in the body, in particular butyrylcholinesterase, which can catalyse the hydrolysis of aromatic amides. The acetamido moiety of Trametinib is readily hydrolysed by these enzymes due to the resonance of the lone pair electrons on the nitrogen atom to the benzene ring, which reduces the energy required to hydrolyse the amide bond. In addition, the hydrolysis product of Trametinib has high cytotoxicity and is prone to the problem of drug resistance (JIANG Jin-fang, LI Xiu-li, CHEN Xiao-yan, ZHONG Da-fang. Role of human liver and intestine esterases in drug design and development[J]. *Acta Pharmaceutica Sinica*, 2018,53(2): 177-185).

The thioamide derivative (in which an oxygen atom of an acetamido moiety is replaced by a sulfur atom) provided by the present disclosure has a higher C—N bond energy due to the larger atomic radius and lower electronegativity of the sulfur atom, which effectively inhibits hydrolysis of an amide structure by AADAC and cholinesterases. This not only reduces the toxicity of such compounds and enhances the MEK kinase activity and anti-tumor activity, but also avoids the drug resistance caused by Trametinib.

In addition, the thioamide derivative provided by the present disclosure is also a hydrogen sulfide donor. In 1996, Abe and Kimura reported on the endogenous generation and signalling capacity of hydrogen sulfide and found that hydrogen sulfide is the third endogenous gas messenger molecule, after nitric oxide and carbon monoxide, which plays an extremely important role in human health. Hydrogen sulfide can quickly cross the cell membrane. It not only has physiological effects such as vasodilation, cardioprotection, anti-inflammatory effects, and antioxidant activity, but also has anti-tumor functions. (Lee ZW, et. al. The slow-releasing hydrogen sulfide donor, GYY4137, exhibits novel anti-cancer effects in vitro and in vivo, *PLOS One*, 2011, 6(6):e21077; Kashfi, K. Anti-cancer activity of new designer hydrogen sulfide-donating hybrids, *Antioxid Redox Signal*, 2014, 20(5):831-846, DOI: 10.1089/ars.2013.5308). The bell-shaped model of anti-tumor activity of hydrogen sulfide has been confirmed to a large extent. (Csaba Szabo, Gasotransmitters in cancer: from pathophysiology to experimental therapy, *Nat Rev Drug Discov*, 2016, 15(3): 185-203, DOI:10.1038/nrd.2015.1; Xu Cao, Lei Ding, et. al. A Review of Hydrogen Sulfide Synthesis, Metabolism, and Measurement: Is Modulation of Hydrogen Sulfide a Novel Therapeutic for Cancer? *Antioxid Redox Signal*, 2019, 31(1): 1-38). The hydrogen sulfide released after hydrolysis of compounds containing the hydrogen sulfide donor structure can not only inhibit the activation of nuclear factor kappa-B (NF-κB), reduce the expression of NF-κB target proteins to induce apoptosis of melanoma B6F10 cells, but also upregulate the expression of Fas-associated death domain protein (FADD) to inhibit the growth of melanoma in the body. (Fangfang Cai, Huangru Xu, et. al. ADT-OH, a hydrogen sulfide-releasing donor, induces apoptosis and inhibits the development of melanoma in vivo by upregulating FADD, *Cell Death Dis.* 2020, 11(1), 33). It has also been reported that hydrogen sulfide can promote glucose uptake by cancer cells, accelerate glycolysis and produce lactate, disrupt acid extrusion within cells and cause acidification of cancer cells, thereby inhibiting cancer cell growth. It can also inhibit mitochondrial function, activate the cell apoptosis pathway, and block the cell cycle at the G1/S phase to exert an anti-tumor effect. (Z-W Lee, X-Y Teo, E Y-W Tay, et. al. Utilizing hydrogen sulfide as a novel anti-cancer agent by targeting cancer glycolysis and pH imbalance, *Br. J. Pharmacol.*, 2014, 171(18), 4322-4336). In addition to inhibiting MEK kinase, the thioamide derivative provided by the present disclosure can also release hydrogen sulfide under the action of enzymes in the body, thereby synergistically enhancing its MEK kinase inhibitory effect and achieving a detoxifying and enhancing effect.

SUMMARY

The objective of this application is to provide a thioamide derivative, and a preparation method and an application thereof. The present application is realized by the following technical solutions.

This application provides a thioamide derivative of general formula (I), or an isomer, a pharmaceutically-acceptable salt, or a prodrug molecule thereof;

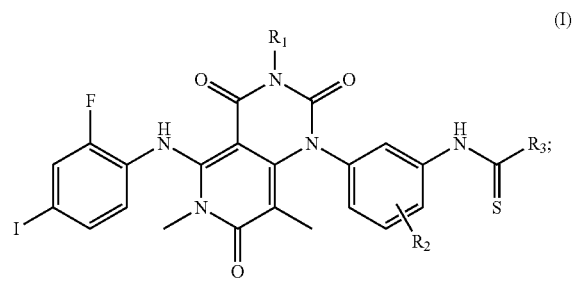

wherein a thioacyl group is attached to an amino group of a benzene ring.

In the general formula (I), $R_1$ is selected from the group consisting of H, $C_1$-$C_{15}$ alkyl, $C_1$-$C_{15}$ alkenyl, $C_1$-$C_{15}$ alkynyl, $C_3$-$C_8$ cycloalkyl group, $C_1$-$C_{15}$ haloalkyl containing 1-6 halogen atoms, $C_1$-$C_{15}$ haloalkenyl containing 1-6 halogen atoms, $C_1$-$C_{15}$ haloalkynyl group containing 1-6 halogen atoms, $C_6$-$C_{20}$ aryl, $C_6$-$C_{20}$ haloaryl, $C_6$-$C_{20}$ phenol, $C_6$-$C_{20}$ polyphenol, $C_1$-$C_{15}$ acyl group, 5-8-membered heterocyclic containing 1-4 heteroatoms, 5-8-membered fused-heterocyclic group containing 1-4 heteroatoms and derivatives thereof.

In the general formula (I), $R_2$ is each independently H, halogen, nitro, cyano, amino or its derivatives; hydroxyl or its derivatives; mercapto or its derivatives; carboxyl or its derivatives; $C_1$-$C_{15}$ alkyl, $C_1$-$C_{15}$ alkenyl, $C_1$-$C_{15}$ alkynyl, $C_1$-$C_{15}$ carbonyl or their derivatives; $C_3$-$C_8$ cycloalkyl or its derivatives; monocyclic or polycyclic aryl containing 6-22 carbons or their derivatives; 5-8-membered heterocyclic or fused-heterocyclic group containing 1-4 heteroatoms or their derivatives; sulfone or sulfoxide or their derivatives; sulfonic acid ester or salt; or phosphate ester or phosphate salt.

In the general formula (I), the number of $R_2$ on the benzene ring is 1-4.

In the general formula (I), $R_3$ is $C_1$-$C_{15}$ alkyl, $C_1$-$C_{15}$ alkenyl, $C_1$-$C_{15}$ alkynyl, or their derivatives; $C_1$-$C_{15}$ haloalkyl, $C_1$-$C_{15}$ haloalkenyl or $C_1$-$C_{15}$ haloalkynyl containing 1-6 halogen atoms, or their derivatives; $C_3$-$C_8$ cycloalkyl or substituted cycloalkyl, or their derivatives; $C_6$-$C_{22}$ aryl, polycyclic aryl or substituted aryl, or their derivatives; 5-8-membered heterocyclic or fused-heterocyclic group containing 1-4 heteroatoms, or their derivatives; $C_1$-$C_{15}$ carboxylic acid, carboxylic acid ester, amide, or their derivatives; $C_1$-$C_{15}$ alcohol containing 1-6 hydroxyl groups, or their derivatives; $C_1$-$C_{15}$ thiol containing 1-6 sulfhydryl groups, or their derivatives; $C_1$-$C_{15}$ amine containing 1-6 amino or amine groups, or their derivatives; $C_1$-$C_{15}$ sulfone or sulfoxide, or their derivatives; $C_1$-$C_{15}$ sulfonic acid ester or salt; or $C_1$-$C_{15}$ phosphate ester or salt.

This application also provides a drug or pharmaceutical composition, comprising a therapeutically effective amount of the thioamide derivative, or an isomer, a pharmaceutically-acceptable salt, or a prodrug thereof.

In some embodiments, the drug or pharmaceutical composition further comprises one or more pharmaceutically-acceptable carriers, diluents or excipients.

The present application also provides a method for preparing the thioamide derivative as shown in the following reaction scheme:

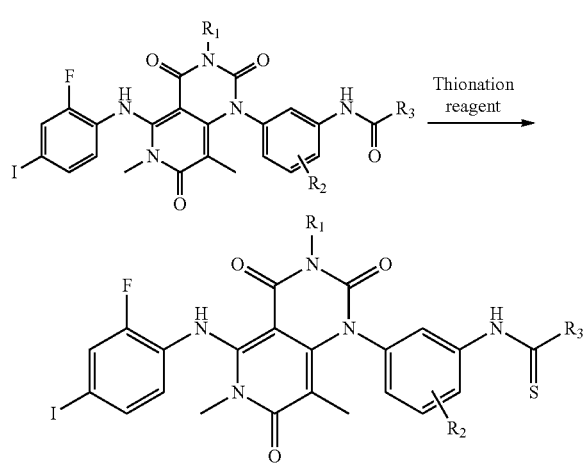

The thionation reagent is selected from the group consisting of P₂S₅, Lawesson's reagent, 2,4-bis(methylthio)-1,3-dithia-2,4-diphosphetane-2,4-disulfide, 2,4-diphenylsulfanyl-1,3-dithia-2,4-diphosphetane-2,4-disulfide, and 2,4-bis(4-phenoxyphenyl)1,3-dithia-2,4-diphosphetane-2,4-disulfide; a solvent used in the sulfuration reaction is a proton solvent, a non-proton solvent or a mixture thereof, such as dichloromethane, dichloroethane, tetrahydrofuran, acetonitrile, ethylene glycol dimethyl ether, 1,4-dioxane, N,N-dimethylformamide, dimethyl sulfoxide, etc.; a temperature of the sulfuration reaction is in a range of −78° C. to 180° C.

The present application also provides another method for preparing the thioamide derivative as shown in the following reaction scheme:

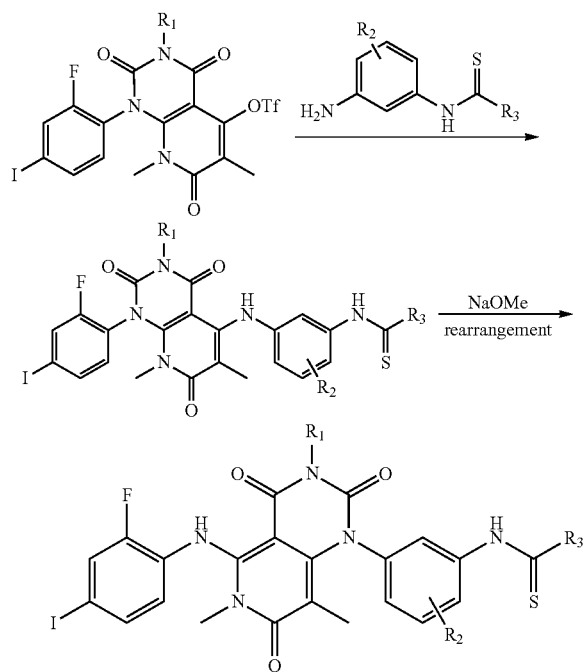

A base used for amino substitution of OTf (Tf is trifluoromethanesulfonyl) is an organic base, which is selected from the group consisting of triethylamine, N,N-diisopropylethylamine, 4-dimethylaminopyridine, 1,8-diazabicyclo[5.4.0]undec-7-ene, 2,6-dimethylpyridine, N-methylmorpholine and N-methylpyrrole; a solvent used for the reaction is a protonic solvent, a non-protonic solvent or a mixture thereof, exemplarily dichloromethane, dichloroethane, tetrahydrofuran, acetonitrile, ethylene glycol dimethyl ether, 1,4-dioxane, N, N-dimethylformamide, N, N-dimethylacetamide, dimethyl sulfoxide, etc.; and a reaction temperature is in a range of −78° C. to 180° C.

A base used in the rearrangement reaction is selected from the group consisting of sodium methoxide, sodium ethoxide, sodium tert-butoxide, lithium carbonate, lithium diisopropylamide and lithium bis(trimethylsilyl)amide. A solvent used in the rearrangement reaction is a protonic solvent, a non-protonic solvent or a mixture thereof, exemplarily methanol, ethanol, isopropanol, tert-butanol, methylene chloride, dichloroethane, tetrahydrofuran, acetonitrile, ethylene glycol dimethyl ether, 1,4-dioxane, N,N-dimethylformamide, N,N-dimethylacetamide, dimethyl sulfoxide, etc.; and a reaction temperature is in a range of −78° C. to 180° C.

The crude product of the sulfuration, substitution and rearrangement reactions can be further purified by solvent extraction method, precipitation method, crystallization method, or purified by column chromatography. A filler of the column can be silica gel, macroporous resin or alumina, and an eluent can be a petroleum ether-acetone mixture, a petroleum ether-ethyl acetate mixture, or a petroleum ether-dichloromethane mixture in different ratios.

In some embodiments, a structure of the thioamide derivative of general formula (I) is selected from the group consisting of:

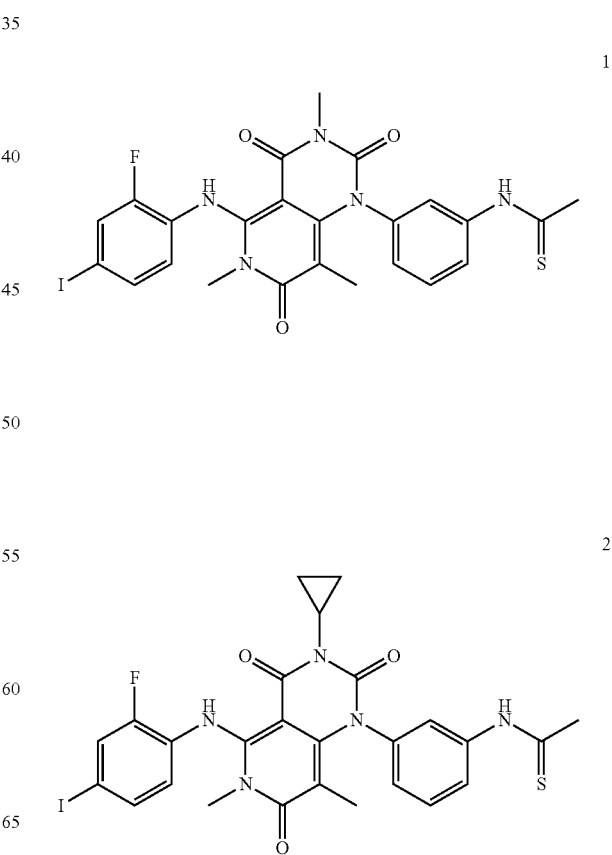

7
-continued
3
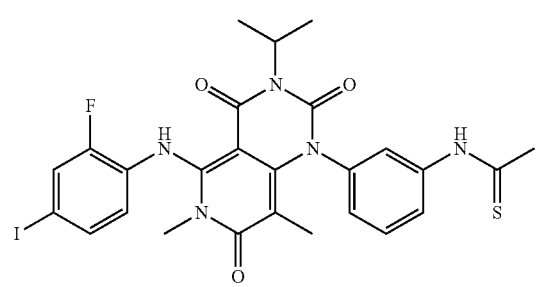
4
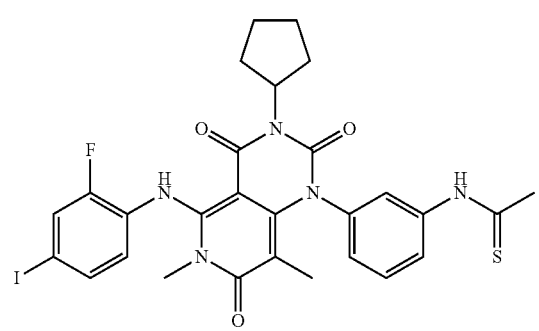
5
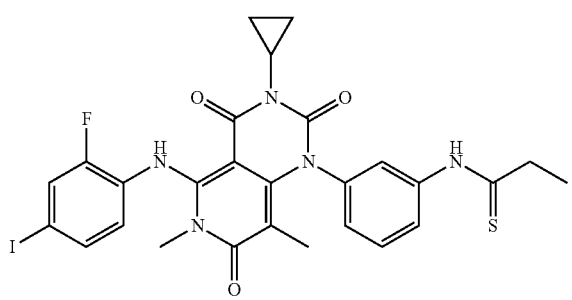
6
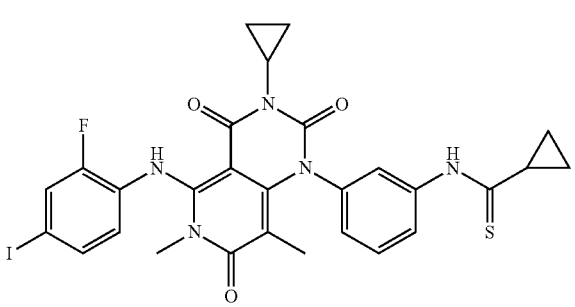
7
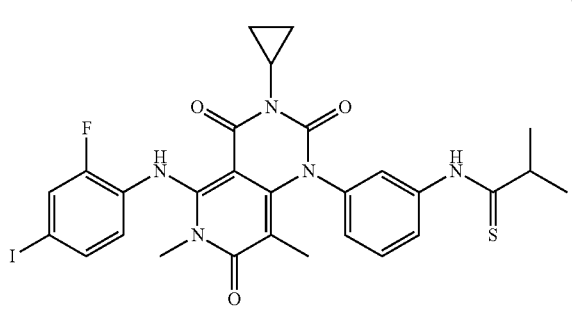
8
-continued
8
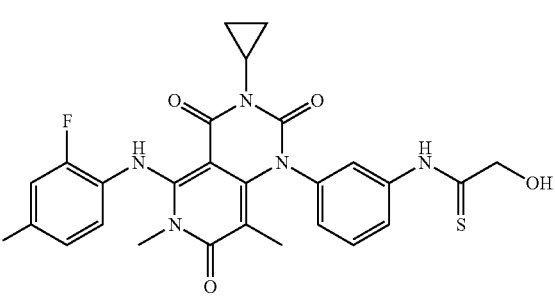
9
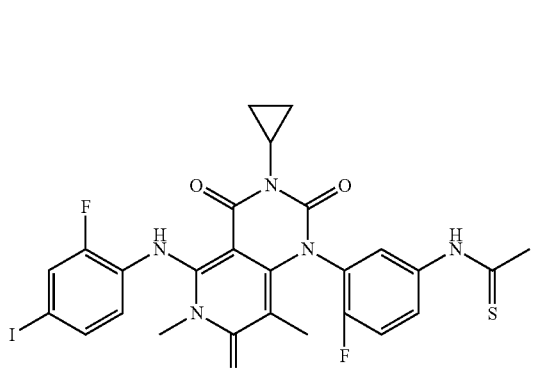
10
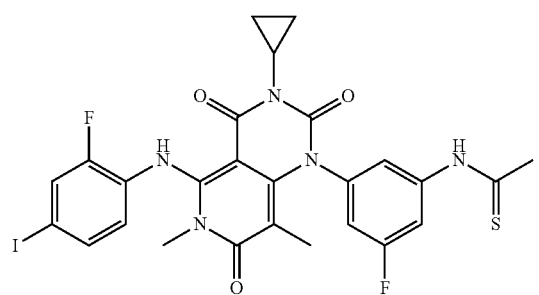
11
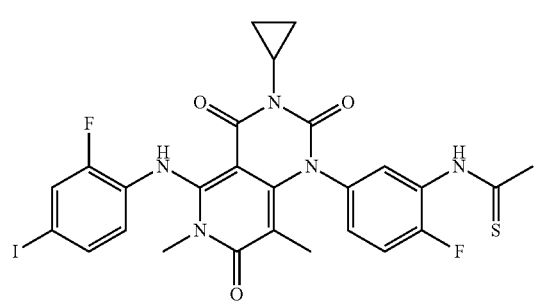
12
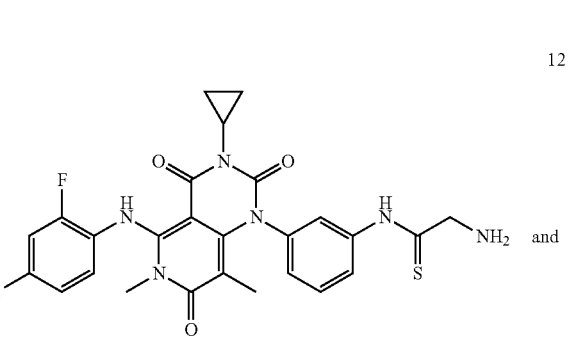
and

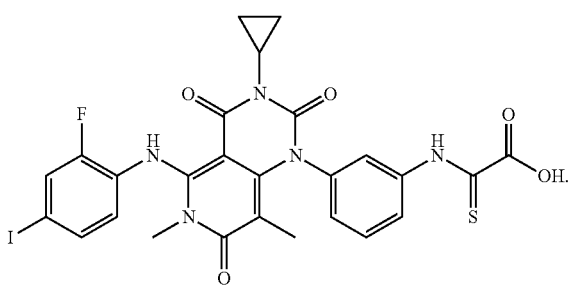

This application also provides an application of a thioamide derivative, or an isomer, a pharmaceutically-acceptable salt, or a prodrug molecule thereof or the drug composition in the preparation of drugs for treating cancer.

In some embodiments, the cancer is brain cancer, glioma, endometrial cancer, ovarian cancer, cervical cancer, breast cancer, colon cancer, lung cancer, prostate cancer, liver cancer, leukemia, lymphoma, skin cancer, basal cell tumor, hemangioma, uterine cancer, laryngeal cancer, gastric cancer, lip cancer, esophageal cancer, nasopharyngeal cancer, gallbladder cancer, pancreatic cancer, kidney cancer, tongue cancer, bladder cancer, melanoma, lipoma, thyroid cancer, thymus cancer or bone cancer.

This application also provides an application of the thioamide derivative, or an isomer, a pharmaceutically-acceptable salt, or a prodrug molecule thereof in the preparation of drugs for treating cancer in combination with one or more anticancer agents.

In some embodiments, the anticancer agent mentioned above is selected from the group consisting of adriamycin, bleomycin, vinblastine, taxane, etoposide, 5-fluorouracil, cyclophosphamide, methotrexate, cisplatin, retinoic acid, temozolomide, dactinomycin, imatinib, gefitinib, sorafenib, erlotinib, sunitinib, afatinib, cabozantinib, osimertinib, rituximab, cetuximab, trastuzumab, nivolumab, pembrolizumab, atezolizumab, durvalumab, avelumab and a combination thereof.

The application has several benefits. Firstly, compared to Trametinib and its analogues, the thioamide derivative effectively inhibits the hydrolysis of aryl acetamide deacetylase and cholinesterase in vivo. This overcomes the issue of resistance to Trametinib. In addition, thioamide derivative can act as a hydrogen sulfide donor which reduces toxicity and enhances the efficacy of anti-tumor drugs. Finally, the thioamide compound defined in this application has lower toxicity, better MEK kinase inhibitory activity, and stronger anti-tumor activity compared with Trametinib. Due to these benefits, the application prospects of these compounds are very broad.

BRIEF DESCRIPTION OF THE DRAWINGS

In order to provide a clearer explanation of the technical solution of the embodiments of the present disclosure, a brief introduction will be given to the accompanying drawings required for the description of the embodiments. It is evident that the accompanying drawings in the following description only show some embodiments of the present disclosure. For those of ordinary skill in the art, other accompanying drawings can be obtained based on these drawings without making any creative effort.

DETAILED DESCRIPTION OF EMBODIMENTS

Figure 1:
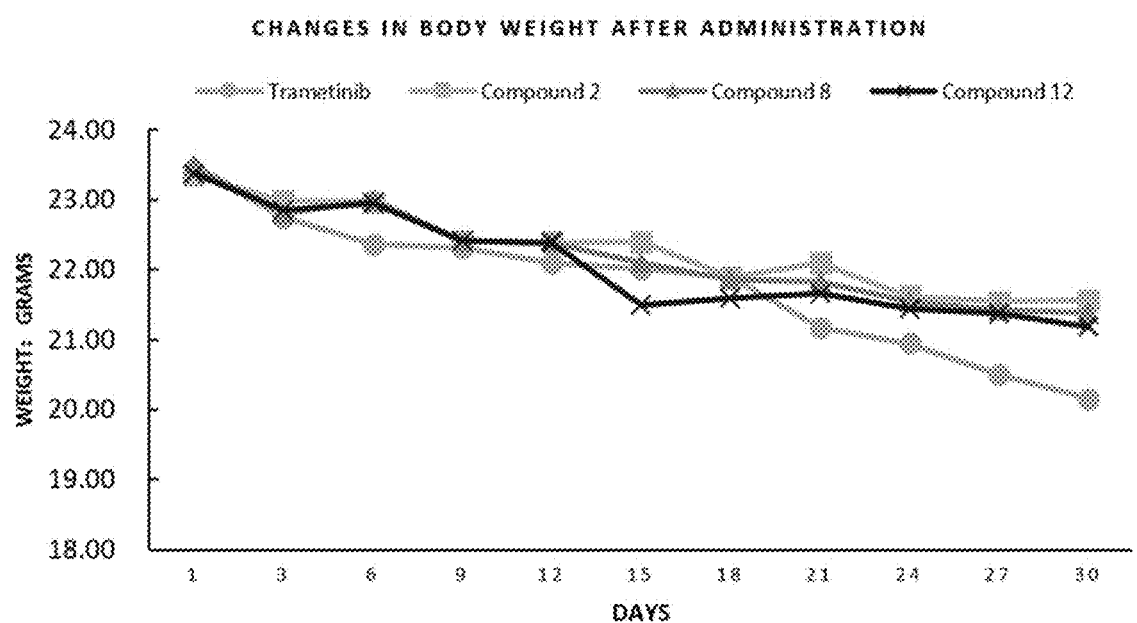
FIG. 1 shows a curve of body weight change in experimental mice described in Example 16 of the present disclosure.

The technical solutions of the present disclosure will be clearly and completely described below in conjunction with the accompanying drawings and embodiments. Obviously, described below are only some embodiments of the present disclosure, instead of all embodiments of the present disclosure. Based on the embodiments in the present disclosure, all other embodiments obtained by those of ordinary skill in the art without making creative efforts shall fall within the scope of the present disclosure.

Example 1 Preparation of Compound 1

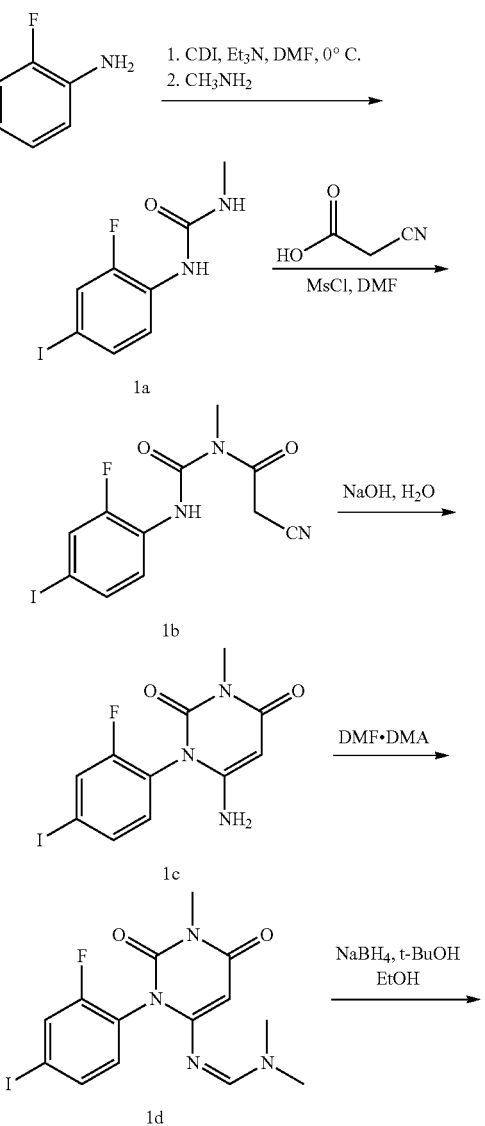

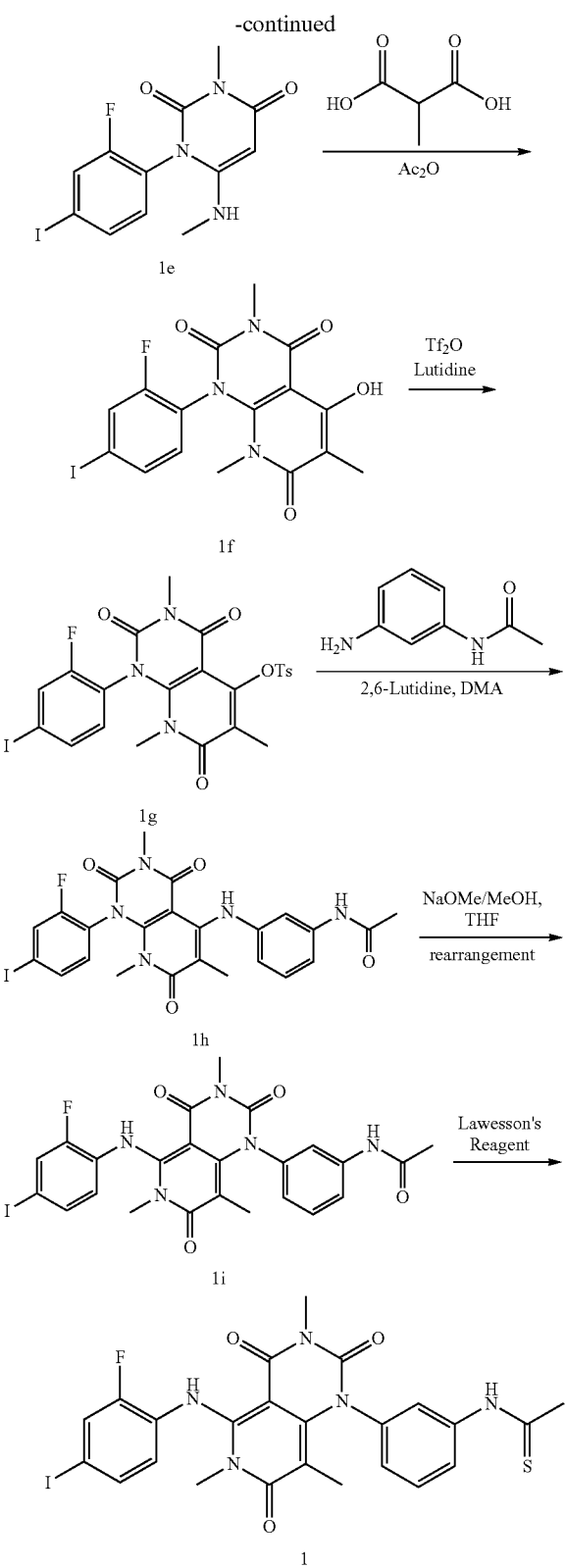

(1) Synthesis of Compound 1a

Under a nitrogen atmosphere, a solution of 2-fluoro-4-iodoaniline (7.48 g, 31.56 mmol) in N,N-dimethylformamide (15 mL) was added dropwise to a mixture of N,N'-carbonyldiimidazole (6.14 g, 37.86 mmol), triethylamine (5.28 mL, 37.98 mmol), methylamine hydrochloride (3.4 g, 50.92 mmol), and N,N-dimethylformamide (30 mL) at 5° C. The temperature of the mixture was slowly raised to room temperature and the mixture was stirred continuously for 8 hours. After the reaction was completed, water (400 mL) was added to quench the reaction, and a large amount of white solid was precipitated. The mixture was stirred for 1 hour, and the precipitate was collected by filtration and dried to give 8.6 g of a white solid as compound 1a (93% yield).

MS(ESI): m/z [M+H]$^+$: 294.9

$^1$H-NMR (400 MHZ, DMSO-d$_6$, δ, ppm): 8.39 (d, J=1.8 Hz, 1H), 7.95 (t, J=8.7 Hz, 1H), 7.56 (dd, J=10.8, 1.9 Hz, 1H), 7.41 (d, J=8.7 Hz, 1H), 6.48 (dd, J=8.8, 4.2 Hz, 1H), 2.64 (d, J=4.6 Hz, 3H).

(2) Synthesis of Compound 1b

Under a nitrogen atmosphere, compound 1a (8.4 g, 28.57 mmol), cyanoacetic acid (4.37 g, 51.42 mmol), and N,N-dimethylformamide (38 mL) were added to a reaction flask and stirred to complete dissolution. At 5° C., methylsulfonyl chloride (5.9 g, 51.42 mmol) was slowly added to the reaction flask. The temperature of the mixture was slowly raised to room temperature, and the mixture was stirred continuously for 8 hours. Water (100 mL) and isopropanol (50 mL) were added dropwise at 5° C. with stirring to quench the reaction. After stirring for 2 hours, the resulting precipitate was collected by filtration and dried to give 8.8 g of a brownish solid as compound 1b (86% yield).

MS(ESI): m/z [M+H]$^+$: 361.9

$^1$H-NMR (400 MHZ, DMSO-d$_6$, δ, ppm): 11.03 (s, 1H), 7.85-7.69 (m, 2H), 7.57 (d, J=8.5 Hz, 1H), 4.42 (s, 2H), 3.20 (s, 3H).

(3) Synthesis of Compound 1c

Compound 1b (8.5 g, 23.54 mmol) and water (50 mL) were mixed, and an aqueous sodium hydroxide solution (2 M 10 mL) was added dropwise. The reaction mixture was stirred at 80° C.-85° C. for 2 hours, cooled to 5° C. and filtered to obtain a precipitate. The precipitate was slurried with 30 mL of isopropyl ether for 2 hours, filtered and dried to give 7.5 g of a white solid as compound 1c (88% yield).

MS(ESI): m/z [M+H]$^+$: 361.9

$^1$H-NMR (400 MHZ, DMSO-d$_6$, δ, ppm): 7.90 (dd, J=9.3, 1.8 Hz, 1H), 7.77-7.69 (m, 1H), 7.27 (t, J=8.2 Hz, 1H), 6.48 (s, 2H), 4.80 (s, 1H), 3.08 (s, 3H).

(4) Synthesis of Compound 1d

Under a nitrogen atmosphere, a mixture of compound 1c (7.3 g, 20.22 mmol), N,N-dimethylformamide dimethyl acetal (DMF-DMA, 7.5 g, 62.68 mmol), and N,N-dimethylformamide (20 mL) was stirred at room temperature for 2.5 hours. Isopropanol (10 mL) and water (50 mL) were added at 5° C. to quench the reaction, and a large amount of solid was precipitated. The reaction mixture was stirred for 1 hour, and the resulting solid was collected by filtration and dried to give 7.2 g of a pale yellow solid as compound 1d (86% yield).

MS(ESI): m/z [M+H]$^+$: 417.0

$^1$H-NMR (400 MHZ, DMSO-d$_6$, δ, ppm): 8.09 (s, 1H), 7.77 (dd, J=9.3, 1.8 Hz, 1H), 7.66-7.59 (m, 1H), 7.15 (t, J=8.1 Hz, 1H), 5.33 (s, 1H), 3.14 (s, 3H), 3.02 (s, 3H), 2.59 (s, 3H).

(5) Synthesis of Compound 1e

Under a nitrogen atmosphere, sodium borohydride (0.96 g, 24.24 mmol) was added batchwise to a mixed solution of ethanol (35 mL) and tert-butanol (70 mL). The mixture was stirred for 1 hour at room temperature. Compound 1d (7 g, 16.83 mmol) was added to the reaction solution at 5° C., and the temperature of the reaction solution was slowly raised to room temperature, and the reaction solution was stirred for 10 hours. 120 mL of water was added at 5° C. to quench the reaction, and the pH was adjusted to 5-6 with an aqueous 10% citric acid solution. The precipitate was collected by filtration and dried to give 4.95 g of a white solid as compound 1e (78% yield).

MS(ESI): m/z [M+H]$^+$: 376.0

$^1$H-NMR (400 MHZ, DMSO-d$_6$, δ, ppm): 7.91 (dd, J=9.3, 1.8 Hz, 1H), 7.73 (dd, J=8.3, 1.1 Hz, 1H), 7.26 (t, J=8.2 Hz, 1H), 6.11 (d, J=4.5 Hz, 1H), 4.72 (s, 1H), 3.10 (s, 3H), 2.57 (d, J=4.5 Hz, 3H).

(6) Synthesis of compound 1f

Under a nitrogen atmosphere, a mixture of compound 1e (4.8 g, 12.8 mmol), methylmalonic acid (2.27 g, 19.2 mmol) and acetic anhydride (5.88 g, 57.6 mmol) was stirred at 105° C. for 4 hours. After the reaction was completed, acetone (15 mL) and water (50 mL) were added at 5° C. to quench the reaction, and the reaction solution was stirred for 1 hour and filtered to obtain a precipitate. The precipitate was slurried with 35 mL of isopropanol for 2 hours, filtered and then dried to give 3.58 g of a gray-white solid as compound 1f (61% yield).

MS(ESI): m/z [M+H]$^+$: 458.0

$^1$-HNMR (400 MHZ, DMSO-d$_6$, δ, ppm): 12.27 (s, 1H), 7.98 (dd, J=9.5, 1.8 Hz, 1H), 7.83-7.69 (m, 1H), 7.27 (t, J=8.1 Hz, 1H), 3.25 (s, 3H), 2.72 (s, 3H), 1.85 (s, 3H).

(7) Synthesis of Compound 1g

Under a nitrogen atmosphere, a mixture of compound 1f (3.2 g, 7.0 mmol), 2,6-dimethylpyridine (1.2 g, 11.2 mmol), and chloroform (30 mL) was stirred to dissolve. Trifluoromethanesulfonic anhydride (3.16 g, 11.2 mmol) was slowly added to the mixture at 5° C. The reaction mixture was stirred for 2 hours at room temperature, washed with 100 mL of water and the aqueous phase was extracted with dichloromethane (100 mL×2). The organic phases were combined, washed with saturated NaCl solution, dried with anhydrous sodium sulfate, concentrated under reduced pressure and purified by silica gel column chromatography (eluent:petroleum ether/ethyl acetate-6:1) to give 3.3 g of a white foamy solid as compound 1g (79% yield).

MS(ESI): m/z [M+H]$^+$: 589.9

$^1$-HNMR (400 MHZ, DMSO-d$_6$, δ, ppm): 7.97 (dd, J=9.5, 1.6 Hz, 1H), 7.73 (dd, J=8.4, 1.4 Hz, 1H), 7.32 (t, J=8.1 Hz, 1H), 3.23 (s, 3H), 2.79 (s, 3H), 2.01 (d, J=15.4 Hz, 3H).

(8) Synthesis of Compound 1h

Under a nitrogen atmosphere, compound 1g (3.2 g, 5.36 mmol), m-aminoacetanilide (0.97 g, 6.43 mmol), and 2,6-dimethylpyridine (1.72 g, 16.1 mmol) were dissolved in N,N-dimethylacetamide (DMA, 40 mL) and stirred at 130° C. for 5 hours. Water (100 mL) and ethyl acetate (100 mL) were added to quench the reaction. The aqueous phase was extracted with ethyl acetate (100 mL×2). The organic phases were combined, washed with saturated NaCl solution, dried with anhydrous sodium sulfate, concentrated under reduced pressure and purified by silica gel column chromatography to give 2.85 g of a white solid as compound 1h (90% yield).

MS(ESI): m/z [M+H]$^+$: 590.1

$^1$-HNMR (400 MHZ, DMSO-d$_6$, δ, ppm): 10.25 (s, 1H), 9.93 (s, 1H), 7.97 (dd, J=9.5, 1.8 Hz, 1H), 7.74 (dd, J=8.4, 1.4 Hz, 1H), 7.34-7.08 (m, 4H), 6.64 (d, J=7.6 Hz, 1H), 3.23 (s, 3H), 2.94 (s, 3H), 2.01 (s, 3H), 1.95 (s, 3H).

(9) Synthesis of Compound 1i

Compound 1h (1.5 g, 2.55 mmol) was dissolved in tetrahydrofuran (20 mL) under a nitrogen atmosphere. A methanol solution of sodium methoxide (30%, 4 mL) was added at 5° C. The reaction mixture was stirred for 2 hours at room temperature. Water (100 mL) was added to quench the reaction. The reaction mixture was extracted twice with ethyl acetate (80 mL×2). The organic phases were combined, washed with saturated NaCl solution, dried with anhydrous sodium sulfate, concentrated under reduced pressure and purified by silica gel column chromatography (eluent:dichloromethane/methanol=80:1) to give 1.2 g of a white solid as compound 1i (81% yield).

MS(ESI): m/z [M+H]$^+$: 590.1

$^1$-HNMR (400 MHZ, DMSO-d$_6$, δ, ppm): 11.21 (s, 1H), 10.11 (s, 1H), 7.78 (dd, J=10.3, 1.6 Hz, 1H), 7.67 (d, J=1.8 Hz, 1H), 7.55 (t, J=7.2 Hz, 2H), 7.37 (t, J=8.1 Hz, 1H), 7.06 (dd, J=7.9, 1.1 Hz, 1H), 6.92 (t, J=8.6 Hz, 1H), 3.20 (s, 3H), 3.08 (s, 3H), 2.04 (s, 3H), 1.26 (s, 3H).

(10) Synthesis of Compound 1

Compound 1i (589 mg, 1.0 mmol) and Lawesson's reagent (1.21 g, 3.0 mmol) were dissolved in tetrahydrofuran (15 mL) under nitrogen atmosphere, and then the reaction solution was heated at 70° C. under reflux for 6 hours. After completion of the reaction, dichloromethane (100 mL) was added and the resulting mixture was washed with saturated aqueous sodium bicarbonate solution (100 mL). The aqueous phase was extracted with dichloromethane (50 mL×2). The organic phases were combined, washed with saturated NaCl solution, dried with anhydrous sodium sulfate, concentrated under reduced pressure and purified by silica gel column chromatography (eluent:petroleum ether/ethyl acetate-3:1) to give 500 mg of a yellow solid as compound 1 (83% yield).

MS(ESI): m/z [M+H]$^+$: 606.0

$^1$-HNMR (400 MHZ, DMSO-d$_6$, δ, ppm): 11.70 (s, 1H), 11.18 (s, 1H), 7.84 (s, 1H), 7.82-7.72 (m, 2H), 7.55 (d, J=8.3 Hz, 1H), 7.48 (t, J=8.0 Hz, 1H), 7.28 (d, J=7.8 Hz, 1H), 6.93 (t, J=8.6 Hz, 1H), 3.21 (s, 3H), 3.08 (s, 3H), 2.60 (s, 3H), 1.30 (s, 3H).

Example 2 Preparation of Compound 2

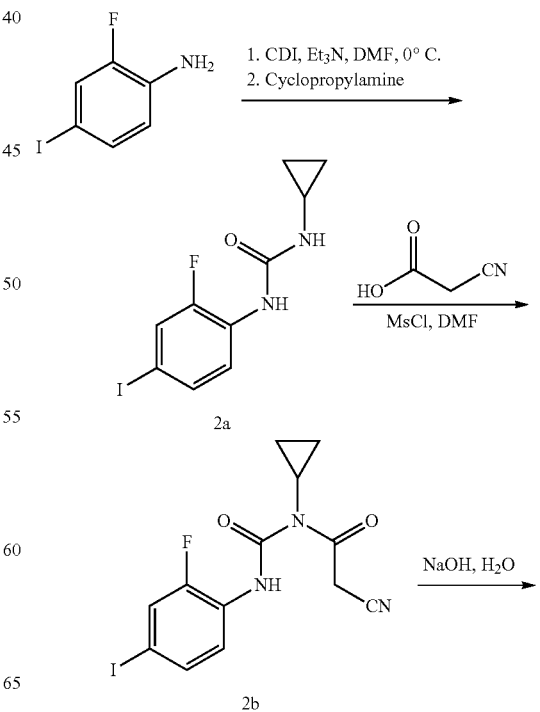

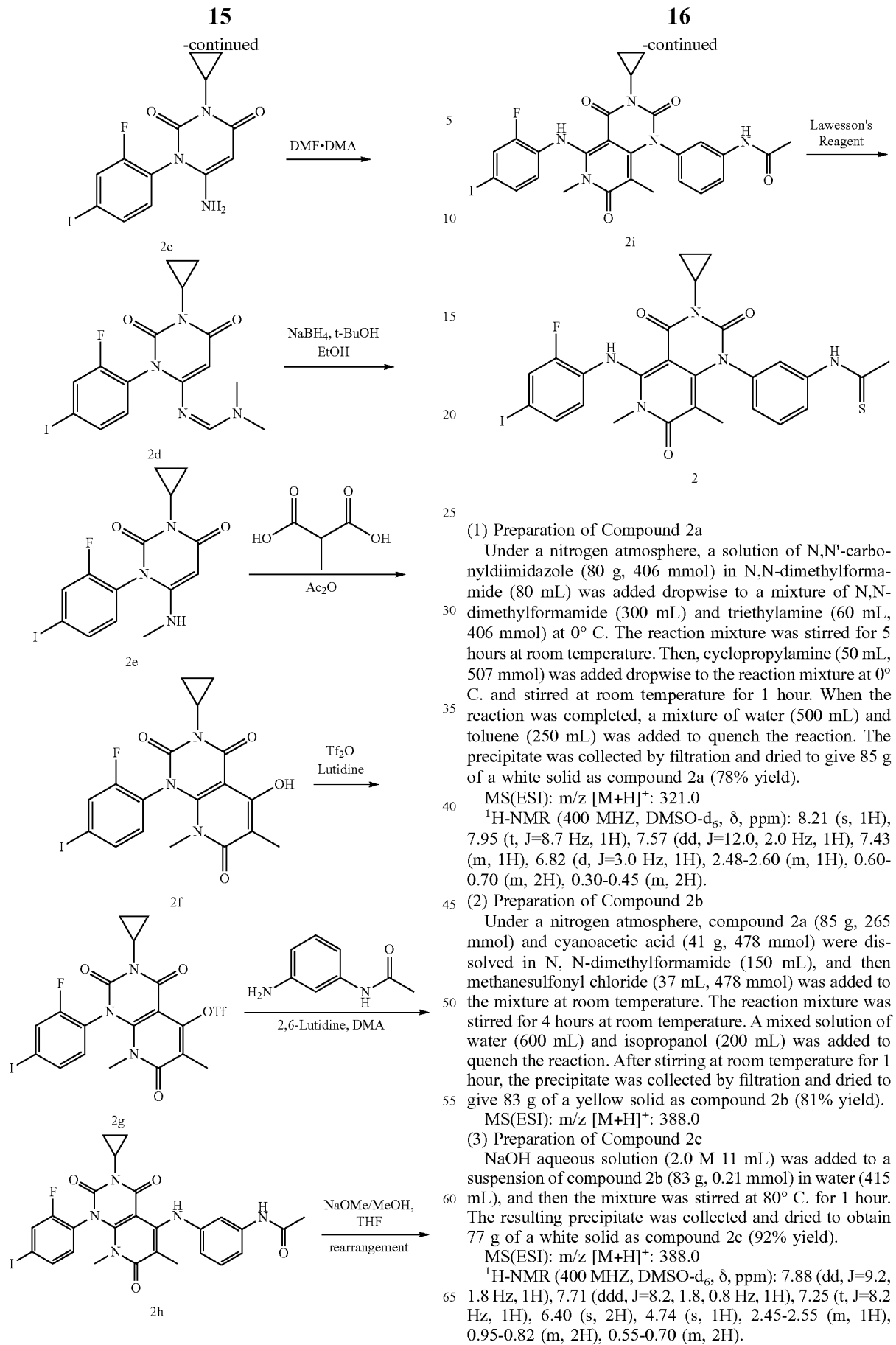

(1) Preparation of Compound 2a

Under a nitrogen atmosphere, a solution of N,N'-carbonyldiimidazole (80 g, 406 mmol) in N,N-dimethylformamide (80 mL) was added dropwise to a mixture of N,N-dimethylformamide (300 mL) and triethylamine (60 mL, 406 mmol) at 0° C. The reaction mixture was stirred for 5 hours at room temperature. Then, cyclopropylamine (50 mL, 507 mmol) was added dropwise to the reaction mixture at 0° C. and stirred at room temperature for 1 hour. When the reaction was completed, a mixture of water (500 mL) and toluene (250 mL) was added to quench the reaction. The precipitate was collected by filtration and dried to give 85 g of a white solid as compound 2a (78% yield).

MS(ESI): m/z [M+H]$^+$: 321.0

$^1$H-NMR (400 MHZ, DMSO-d$_6$, δ, ppm): 8.21 (s, 1H), 7.95 (t, J=8.7 Hz, 1H), 7.57 (dd, J=12.0, 2.0 Hz, 1H), 7.43 (m, 1H), 6.82 (d, J=3.0 Hz, 1H), 2.48-2.60 (m, 1H), 0.60-0.70 (m, 2H), 0.30-0.45 (m, 2H).

(2) Preparation of Compound 2b

Under a nitrogen atmosphere, compound 2a (85 g, 265 mmol) and cyanoacetic acid (41 g, 478 mmol) were dissolved in N, N-dimethylformamide (150 mL), and then methanesulfonyl chloride (37 mL, 478 mmol) was added to the mixture at room temperature. The reaction mixture was stirred for 4 hours at room temperature. A mixed solution of water (600 mL) and isopropanol (200 mL) was added to quench the reaction. After stirring at room temperature for 1 hour, the precipitate was collected by filtration and dried to give 83 g of a yellow solid as compound 2b (81% yield).

MS(ESI): m/z [M+H]$^+$: 388.0

(3) Preparation of Compound 2c

NaOH aqueous solution (2.0 M 11 mL) was added to a suspension of compound 2b (83 g, 0.21 mmol) in water (415 mL), and then the mixture was stirred at 80° C. for 1 hour. The resulting precipitate was collected and dried to obtain 77 g of a white solid as compound 2c (92% yield).

MS(ESI): m/z [M+H]$^+$: 388.0

$^1$H-NMR (400 MHZ, DMSO-d$_6$, δ, ppm): 7.88 (dd, J=9.2, 1.8 Hz, 1H), 7.71 (ddd, J=8.2, 1.8, 0.8 Hz, 1H), 7.25 (t, J=8.2 Hz, 1H), 6.40 (s, 2H), 4.74 (s, 1H), 2.45-2.55 (m, 1H), 0.95-0.82 (m, 2H), 0.55-0.70 (m, 2H).

(4) Preparation of Compound 2d

Under a nitrogen atmosphere, compound 2c (77 g, 198 mmol), DMF-DMA (74 mL, 497 mmol) and N,N-dimethylformamide (150 mL) were added sequentially to a reaction flask and stirred at room temperature for 2 hours. Isopropanol (80 mL) and water (500 mL) were added dropwise in sequence to quench the reaction at a temperature not exceeding room temperature. The reaction mixture was stirred for 1 hour at room temperature. The precipitate was collected by filtration and dried to give 81 g of a pale solid as compound 2d (92% yield).

MS(ESI): m/z [M+H]$^+$: 442.8

$^1$H-NMR (400 MHZ, DMSO-d$_6$, δ, ppm): 8.04 (s, 1H), 7.75 (dd, J=9.2, 1.9 Hz, 1H), 7.66-7.52 (m, 1H), 7.14 (t, J=8.1 Hz, 1H), 5.24 (s, 1H), 3.01 (s, 3H), 2.58 (s, 3H), 2.50-2.60 (m, 1H), 0.98-0.85 (m, 2H), 0.75-0.61 (m, 2H).

(5) Preparation of Compound 2e

Under a nitrogen atmosphere, sodium borohydride (10.39 g, 274 mmol) was added batchwise to a mixed solution of ethanol (150 mL) and tert-butanol (300 mL), and stirred at room temperature for 1 hour. Compound 2d (81 g, 183 mmol) was added batchwise to the reaction solution at a temperature not exceeding 10° C. The temperature of the reaction solution was raised to room temperature, and the reaction solution was stirred continuously for 2.5 hours. The reaction was quenched at 5° C. with water (365 mL) and aqueous 10% citric acid solution (283 mL). The reaction mixture was stirred for 3 hours at 5° C. The precipitate was collected by filtration and dried to give 50 g of a pale solid as compound 2e (68% yield).

MS(ESI): m/z [M+H]$^+$: 402.0

$^1$H-NMR (400 MHZ, DMSO-d$_6$, δ, ppm): 7.89 (dd, J=9.3, 1.9 Hz, 1H), 7.72 (dd, J=8.2, 1.9 Hz, 1H), 7.24 (t, J=8.2 Hz, 1H), 6.03 (q, J=4.5 Hz, 1H), 4.64 (s, 1H), 2.54 (d, J=4.5 Hz, 3H), 2.45-2.51 (m, 1H), 0.96-0.83 (m, 2H), 0.55-0.70 (m, 2H).

(6) Preparation of Compound 2f

Under a nitrogen atmosphere, compound 2e (50 g, 125 mmol), methylmalonic acid (22 g, 187 mmol) and acetic anhydride (50 mL) were added sequentially to a reaction flask and heated at 100° C. with stirring for 3 hours. After the reaction was completed, the reaction solution was cooled to 50° C. Acetone (100 mL) was added dropwise and stirred for 0.5 hours, and then water (250 mL) was added to quench the reaction. The reaction solution was stirred at 5° C. for 1 hour and filtered to obtain a precipitate. The precipitate was slurried with isopropanol (133 mL) at room temperature for 4 hours, filtered and then dried to give 32 g of a pale solid as compound 2f (57% yield).

MS(ESI): m/z [M+H]$^+$: 484.0

$^1$H-NMR (400 MHZ, DMSO-d$_6$, δ, ppm): 12.26 (s, 1H), 7.96 (dd, J=9.4, 1.9 Hz, 1H), 7.73 (dd, J=8.4, 1.9 Hz, 1H), 7.24 (t, J=8.1 Hz, 1H), 2.55-2.65 (m, 4H), 1.84 (s, 3H), 1.11-0.94 (m, 2H), 0.83-0.64 (m, 2H).

(7) Preparation of Compound 2g

Under a nitrogen atmosphere, compound 2f (32 g, 72 mmol), 2,6-dimethylpyridine (10 mL, 87 mmol) and chloroform (165 mL) were added sequentially to a reaction flask. Trifluoromethanesulfonic anhydride (13 mL, 79 mmol) was added dropwise to the reaction mixture at 5° C. and stirred at room temperature for 2 hours. The reaction was quenched with saturated aqueous sodium bicarbonate solution (165 mL), and the resulting mixture was washed with saturated NaCl solution (165 mL). The organic phase was dried with anhydrous sodium sulfate and concentrated under reduced pressure. The residue obtained was recrystallized with isopropanol (200 mL) to give 22 g of a white solid as compound 2g (60% yield).

MS(ESI): m/z [M+H]hu +: 616.0

$^1$H-NMR (400 MHZ, DMSO-d$_6$, δ, ppm): 7.95 (dd, J=9.5, 1.9 Hz, 1H), 7.72 (dd, J=8.4, 1.9 Hz, 1H), 7.31 (t, J=8.1 Hz, 1H), 2.76 (s, 3H), 2.65-2.74 (m, 1H), 2.02 (s, 3H), 0.95-1.14 (m, 2H), 0.68-0.54 (m, 2H).

(8) Preparation of Compound 2h

Under a nitrogen atmosphere, a mixture of compound 2g (3.3 g, 5.36 mmol), m-aminoacetanilide (0.97 g, 6.43 mmol), 2,6-dimethylpyridine (1.72 g, 16.1 mmol) and DMA (40 mL) was stirred at 130° C. for 5 hours. At the end of the reaction, water (200 mL) was added and the reaction mixture was extracted with ethyl acetate (100 mL×2). The organic phases were combined, washed with saturated NaCl solution, dried with anhydrous sodium sulfate, concentrated under reduced pressure, and purified by silica gel column chromatography (eluent:dichloromethane/methanol=80:1) to give 2.86 g of a white solid as compound 2h (87% yield).

MS(ESI): m/z [M+H]$^+$: 616.1

(9) Preparation of Compound 2i

Under a nitrogen atmosphere, a methanol solution of sodium methoxide (4 mL, 30%, 22.2 mmol) was added dropwise to a tetrahydrofuran solution (20 mL) of compound 2h (1.5 g, 2.44 mmol) at 5° C. The reaction mixture was stirred for 2 hours at room temperature. Water (100 mL) was added to quench the reaction. The reaction mixture was extracted with ethyl acetate (100 mL×2). The organic phases were combined, washed with saturated NaCl solution, dried with anhydrous sodium sulfate, concentrated under reduced pressure and purified by silica gel column chromatography (eluent:dichloromethane/methanol=80:1) to give 1.2 g of a white solid as compound 2i (81.2% yield).

MS(ESI): m/z [M+H]$^+$: 616.1

$^1$H-NMR (400 MHZ, DMSO-d$_6$, δ, ppm): 11.21 (s, 1H), 10.11 (s, 1H), 7.78 (dd, J=10.3, 1.9 Hz, 1H), 7.57-7.67 (m, 3H), 7.37 (t, J=8.1 Hz, 1H), 7.02-7.08 (m, 1H), 6.92 (t, J=8.6 Hz, 1H), 3.07 (s, 3H), 2.56-2.68 (m, 1H), 2.04 (s, 3H), 1.26 (s, 3H), 0.90-1.00 (m, 2H), 0.60-0.72 (m, 2H).

(10) Preparation of Compound 2

Compound 2i (615 mg, 1.0 mmol) and Lawesson's reagent (1.21 g, 3.0 mmol) were dissolved in 1,4-dioxane (10 mL) under a nitrogen atmosphere and stirred at 100° C. for 2 hours. When the reaction was complete, ethyl acetate (100 mL) was added into the reaction mixture. The organic phase was washed with saturated aqueous sodium bicarbonate solution (100 mL) and saturated NaCl solution (100 mL), dried with anhydrous sodium sulfate, concentrated under reduced pressure and purified by silica gel column chromatography (eluent:petroleum ether/ethyl acetate=3:1) to give 510 mg of a light yellow solid as compound 2 (81% yield).

MS(ESI): m/z [M+H]$^+$: 632.1

$^1$H-NMR (400 MHZ, DMSO-d$_6$, δ, ppm): 11.70 (s, 1H), 11.07 (s, 1H), 7.70-7.90(m, 3H), 7.55 (d, J=8.4 Hz, 1H), 7.48 (t, J=8.0 Hz, 1H), 7.25 (d, J=8.0 Hz, 1H), 6.93 (t, J=8.4 Hz, 1H), 3.08 (s, 3H), 2.61 (s, 3H), 2.59-2.66(m, 1H), 1.29 (s, 3H), 0.90-1.00 (m, 2H), 0.64-0.72 (m, 2H).

Example 3 Preparation of Compound 3

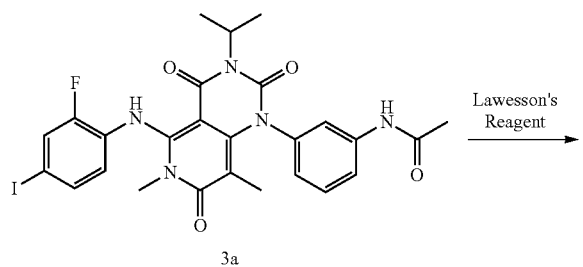

3a

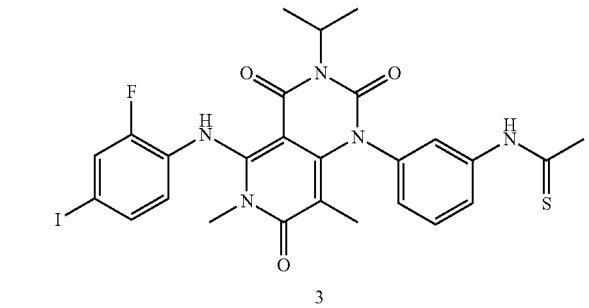

3

By a method similar to that described in examples 1 and 2 above, compound 3a was synthesized as the starting material for the preparation of compound 3.

Under a nitrogen atmosphere, compound 3a (500 mg, 0.81 mmol) and Lawesson's reagent (982.7 mg, 2.43 mmol) were dissolved in tetrahydrofuran (15 mL), and heated at 70° C. under reflux for 3 hours. At the end of the reaction, ethyl acetate (50 mL) was added and the resulting mixture was washed with saturated aqueous sodium bicarbonate solution (100 mL). The aqueous phase was extracted with ethyl acetate (50 mL×2). The organic phases were combined, washed with saturated NaCl solution, dried with anhydrous sodium sulfate, concentrated under reduced pressure and purified by silica gel column chromatography (eluent:petroleum ether/ethyl acetate/=2-3:1) to give 431 g of a yellow solid as compound 3 (84% yield).

MS(ESI): m/z [M+H]$^+$: 634.1

$^1$H-NMR (400 MHZ, DMSO-d$_6$, δ, ppm): 11.69 (s, 1H), 11.19 (s, 1H), 7.93 -7.67 (m, 3H), 7.55 (d, J=8.2 Hz, 1H), 7.47 (t, J=8.0 Hz, 1H), 7.27 (d, J=7.7 Hz, 1H), 6.94 (t, J=8.5 Hz, 1H), 4.95 (dt, J=13.6, 6.7 Hz, 1H), 3.07 (s, 3H), 2.59 (s, 3H), 1.38 (d, J=6.8 Hz, 6H), 1.28 (s, 3H).

Example 4 Preparation of Compound 4

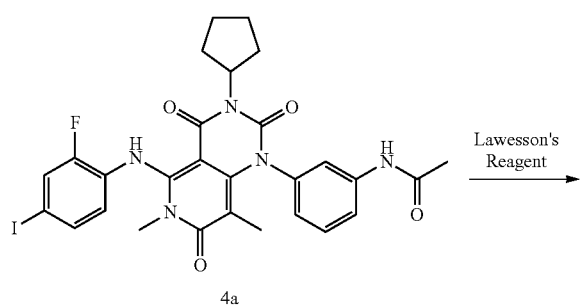

4a

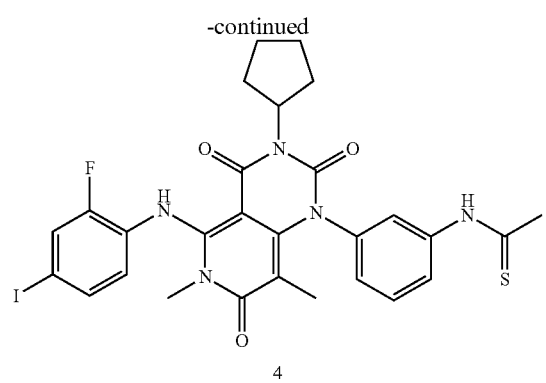

4

By a method similar to that described in examples 1 and 2, compound 4a was synthesized as the starting material for the preparation of compound 4.

Under a nitrogen atmosphere, compound 4a (578.8 mg, 0.9 mmol) and Lawesson's reagent (1.09 g, 2.7 mmol) were dissolved in tetrahydrofuran (30 mL), and heated at 70° C. under reflux for 3 hours. At the end of the reaction, ethyl acetate (300 mL) was added and the resulting mixture was washed with saturated aqueous sodium bicarbonate solution (100 mL). The aqueous phase was extracted with ethyl acetate (100 mL×2). The organic phases were combined, washed with saturated NaCl solution, dried with anhydrous sodium sulfate, concentrated under reduced pressure and purified by silica gel column chromatography (eluent:petroleum ether/ethyl acetate-2-3:1) to give 480 mg of a pale yellow solid as compound 4 (81% yield).

MS(ESI): m/z [M+H]$^+$: 660.1

$^1$H-NMR (400 MHZ, DMSO-d$_6$, δ, ppm): 11.66 (s, 1H), 11.14 (s, 1H), 7.76 (dd, J=15.9, 10.1 Hz, 3H), 7.51 (d, J=8.3 Hz, 1H), 7.44 (t, J=8.0 Hz, 1H), 7.25 (d, J=7.9 Hz, 1H), 6.90 (t, J=8.6 Hz, 1H), 5.17-5.01 (m, 1H), 3.04 (s, 3H), 2.57 (s, 3H), 2.00-1.90 (m, 2H), 1.85-1.70 (m, 4H), 1.60-1.40 (m, 2H), 1.26 (s, 3H).

Example 5 Preparation of Compound 5

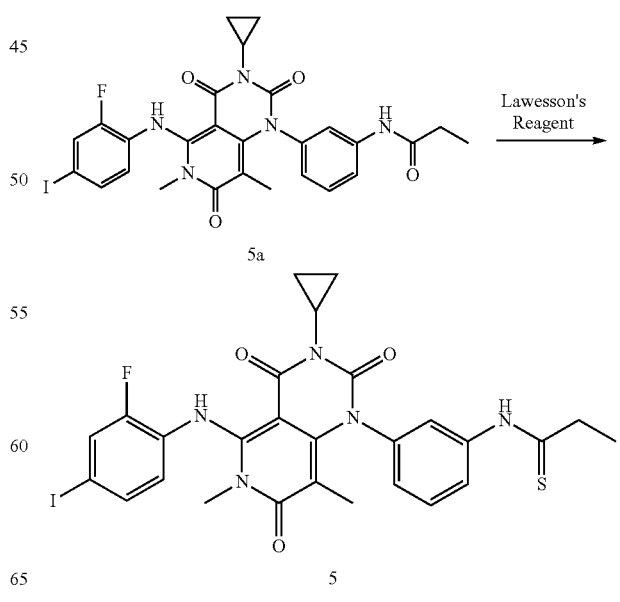

Compound 5a was synthesized as a starting material for the preparation of compound 5 by a method similar to that described in examples 1 and 2.

Under a nitrogen atmosphere, compound 5a (600 mg, 0.95 mmol) and Lawesson's reagent (771 g, 1.91 mmol) were dissolved in 1,4-dioxane (10 mL) and heated at 100° C. for 2 hours. At the end of the reaction, the reaction mixture was concentrated and purified by silica gel column chromatography (eluent:petroleum ether/ethyl acetate=1-2:1) to give 500 mg of a light yellow solid as compound 5 (80% yield).

MS(ESI): m/z [M+H]$^+$: 646.1

$^1$H-NMR (400 MHZ, DMSO-d$_6$, δ, ppm): 11.62 (s, 1H), 11.06 (s, 1H), 7.70-7.90 (m, 3H), 7.55 (d, J=8.3 Hz, 1H), 7.47 (t, J=8.0 Hz, 1H), 7.25 (d, J=9.0 Hz, 1H), 6.92 (t, J=8.6 Hz, 1H), 3.08 (s, 3H), 2.74 (q, J=7.4 Hz, 2H), 2.52-2.66 (m, 1H), 1.29 (s, 3H), 1.26 (t, J=7.4 Hz, 3H), 0.85-0.95 (m, 2H), 0.60-0.70 (m, 2H).

Example 6 Preparation of Compound 6

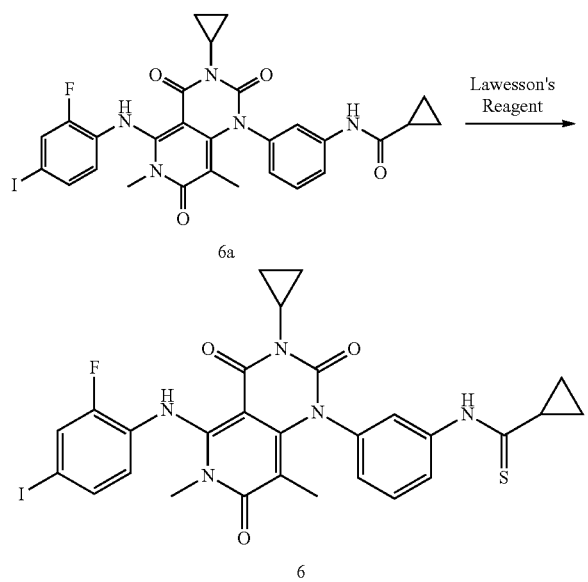

Compound 6a was synthesized as a starting material for the preparation of compound 6 by a method similar to that described in examples 1 and 2.

Under a nitrogen atmosphere, compound 6a (700 mg, 1.09 mmol) and Lawesson's reagent (881 g, 2.18 mmol) were dissolved in 1,4-dioxane (10 mL) and heated at 100° C. for 2 hours. At the end of the reaction, the reaction mixture was concentrated and purified by silica gel column chromatography (eluent:petroleum ether/ethyl acetate=1-2:1) to give 600 mg of a light yellow solid as compound 6 (80% yield).

MS(ESI): m/z [M+H]$^+$: 658.1

$^1$H-NMR (400 MHZ, DMSO-d$_6$, δ, ppm): 11.82 (s, 1H), 11.06 (s, 1H), 7.70-7.90 (m, 3H), 7.55 (d, J=8.4 Hz, 1H), 7.46 (d, J=8.0 Hz, 1H), 7.25 (d, J=9.0 Hz, 1H), 6.92 (t, J=8.6 Hz, 1H), 3.07 (s, 3H), 2.55-2.70 (m, 1H), 2.20-2.35 (m, 1H), 1.30 (s, 3H), 1.05-1.20 (m, 2H), 0.75-0.90 (m, 4H), 0.55-0.70 (m, 2H).

Example 7 Preparation of Compound 7

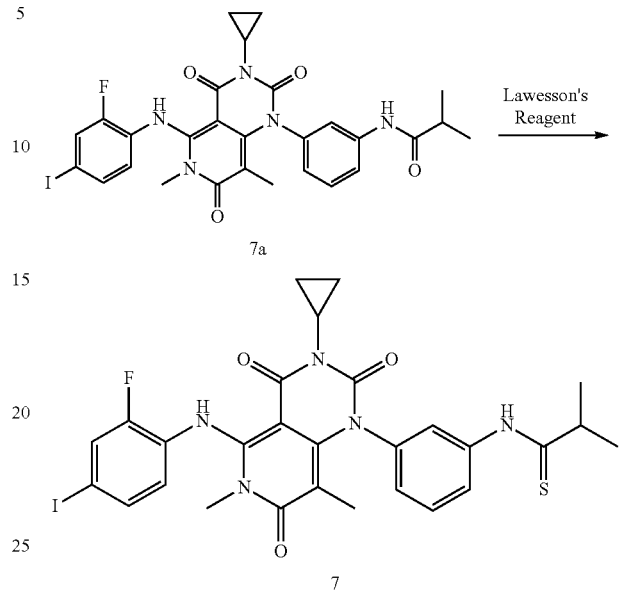

Compound 7a was synthesized as a starting material for the preparation of compound 7 by a method similar to that described in examples 1 and 2.

Under a nitrogen atmosphere, compound 7a (800 mg, 1.24 mmol) and Lawesson's reagent (1.0 g, 2.48 mmol) were dissolved in 1,4-dioxane (15 mL) and heated at 100° C. for 2 hours. At the end of the reaction, the reaction mixture was concentrated and purified by silica gel column chromatography (eluent:petroleum ether/ethyl acetate=1-2:1) to give 680 mg of a light yellow solid as compound 7 (84% yield).

MS(ESI): m/z [M+H]$^+$: 660.1

$^1$H-NMR (400 MHZ, DMSO-d$_6$, δ, ppm): 11.56 (s, 1H), 11.08 (s, 1H), 7.65-7.85 (m, 3H), 7.55 (d, J=8.0 Hz, 1H), 7.47 (t, J=8.0 Hz, 1H), 7.20-7.30 (m, 1H), 6.92 (t, J=8.4 Hz, 1H), 3.08 (s, 3H), 2.95-3.20 (m, 1H), 2.50-2.70 (m, 1H), 1.47 (s, 3H), 1.21 and 1.20 (2s, 6H), 0.80-1.00 (m, 2H), 0.55-0.75 (m, 2H).

Example 8 Preparation of Compound 8

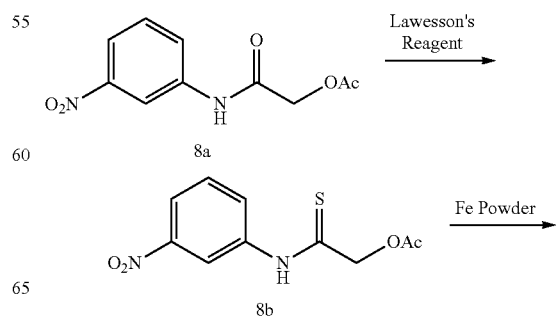

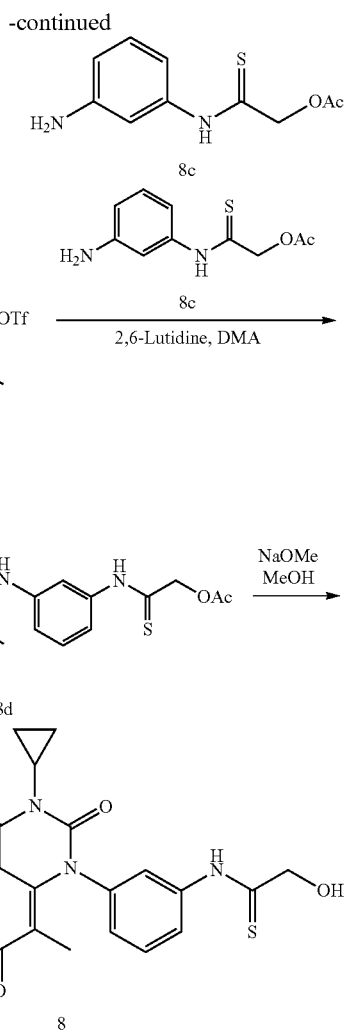

(1) Synthesis of Compound 8b

Under a nitrogen atmosphere, compound 8a (2.31 g, 9.7 mmol, 1.0 eq) and Lawesson's reagent (3.92 g, 9.7 mmol, 1.0 eq) were dissolved in anhydrous tetrahydrofuran (25 mL) and stirred at 70° C. for 12 hours. At the end of the reaction, saturated aqueous sodium bicarbonate solution (25 mL) was added to quench the reaction. The reaction mixture was extracted with ethyl acetate (25 mL×3). The organic phases were combined, washed with saturated NaCl solution, dried with anhydrous sodium sulfate, concentrated under reduced pressure and purified by silica gel column chromatography (eluent:petroleum ether/ethyl acetate=4:1) to give 2.18 g of a yellow solid as compound 8b (88.5% yield).

MS(+ESI): m/z [M+H]$^+$=255.0

$^1$H NMR (400 MHZ, DMSO-d$_6$, δ, ppm): 11.83 (s, 1H), 8.81 (t, J=2.1 Hz, 1H), 8.15 (m, 2H), 7.72 (t, J=8.2 Hz, 1H), 4.95 (s, 2H), 2.16 (s, 3H).

(2) Synthesis of Compound 8c

A mixture of compound 8b (1 g, 3.94 mmol, 1.0 eq), ethanol (7.5 mL), aqueous saturated ammonium chloride solution (7.5 mL) and iron powder (1.1 g, 19.7 mmol, 5.0 eq) was stirred under reflux at 90° C. for 10 minutes under a nitrogen atmosphere. At the end of the reaction, the reaction mixture was cooled to room temperature and filtered to remove the iron powder. Water (25 mL) was added to the filtrate and then the filtrate was extracted with dichloromethane (25 mL×3). The organic phases were combined, washed with saturated NaCl solution, dried with anhydrous sodium sulfate, concentrated under reduced pressure and dried under vacuum to give 0.81 g of a white crude product as compound 8c. The crude product was used directly for the next step without purification.

MS(+ESI): m/z [M+1]$^+$=225.1

$^1$H NMR (400 MHZ, DMSO, δ, ppm): 11.29 (s, 1H), 7.02 (t, J=8.0 Hz, 1H), 6.93 (t, J=2.1 Hz, 1H), 6.79 (m, 1H), 6.46 (m, 1H), 5.22 (s, 2H), 4.87 (s, 2H), 2.13 (s, 3H).

(3) Synthesis of Compounds 8d

A mixture of compound 8c (810 mg, 3.62 mmol, 1.0 eq), compound 2g (2.34 g, 3.8 mmol, 1.05 eq), 2,6-dimethylpyridine (780 mg, 7.23 mmol, 2.0 eq) and DMA (6.5 mL) was stirred at 130° C. for 2 hours. The reaction was quenched with aqueous citric acid solution (25 mL). The mixture was extracted with dichloromethane (25 mL×3). The organic phases were combined, washed with saturated NaCl solution, dried with anhydrous sodium sulfate, concentrated under reduced pressure and purified by silica gel column chromatography (eluent:petroleum ether/ethyl acetate=3:2) to give 2.3 g of a yellow solid as compound 8d (84.3% yield).

MS(+ESI): m/z [M+1]$^+$=690.1

$^1$H NMR (400 MHZ, DMSO-d$_6$, δ, ppm): 11.52 (s, 1H), 10.17 (s, 1H), 7.95 (dd, J=9.4, 1.8 Hz, 1H), 7.73 (dd, J=8.4, 1.4 Hz, 1H), 7.57-7.06 (m, 4H), 6.89 (d, J=7.9 Hz, 1H), 4.89 (s, 2H), 2.72 (d, J=22.1 Hz, 3H), 2.66 (m, 1H), 2.13 (s, 3H), 1.59 (d, J=9.4 Hz, 3H), 1.08-0.91 (m, 2H), 0.81-0.54 (m, 2H).

(4) Synthesis of Compound 8

Compound 8d (1.72 g, 2.5 mmol, 1.0 eq) was dissolved in tetrahydrofuran (100 mL) under a nitrogen atmosphere. A methanol solution of sodium methoxide (5 mL, 30%) was slowly added. The reaction mixture was stirred for 0.5 hours at room temperature. At the end of the reaction, ethyl acetate (100 mL) was added and the resulting mixture was washed with aqueous citric acid solution (100 mL). The organic phase was washed with saturated NaCl solution, dried with anhydrous sodium sulfate, concentrated under reduced pressure and purified by silica gel column chromatography (eluent:petroleum ether/ethyl acetate=1-2:1) to give 412 mg of pale yellow solid as compound 8 (25.5% yield).

MS(+ESI): m/z [M+1]$^+$=648.0

$^1$H NMR (400 MHZ, DMSO, δ, ppm): 11.34 (s, 1H), 11.05 (s, 1H), 7.76-7.90 (m, 3H), 7.55 (d, J=8.0 Hz, 1H), 7.48 (t, J=8.0 Hz, 1H), 7.28 (d, J=6.8 Hz, 1H), 6.93 (t, J=8.6 Hz, 1H), 4.33 (s, 2H), 3.08 (s, 3H), 2.55-2.70 (m, 1H), 1.31 (s, 3H), 0.90-1.00 (m, 2H), 0.60-0.70 (m, 2H).

Example 9 Preparation of Compound 9

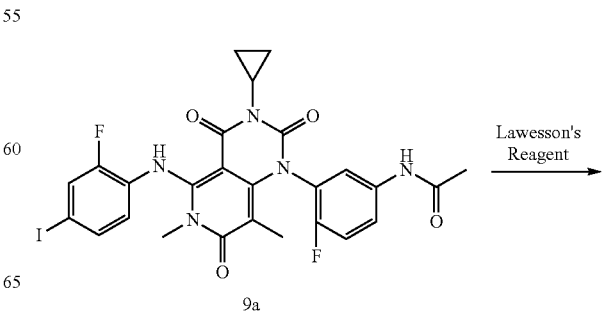

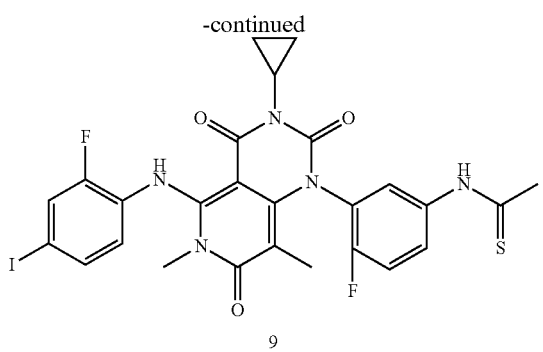

9

Compound 9a was synthesized as a starting material for the preparation of compound 9 by a method similar to examples 1 and 2.

Under a nitrogen atmosphere, a tetrahydrofuran solution (20 mL) of compound 9a (800 mg, 1.26 mmol) and Lawesson's reagent (1.0 g, 2.48 mmol) was heated at 70° C. for 3 hours. At the end of the reaction, the reaction mixture was concentrated and purified by silica gel column chromatography (eluent:petroleum ether/ethyl acetate=1-2:1) to give 664 mg of a light yellow solid as compound 9 (81% yield).

MS(ESI): m/z [M+H]$^+$: 649.8

$^1$H NMR (400 MHZ, DMSO-d$_6$, δ, ppm): 11.67 (s, 1H), 11.06 (s, 1H), 7.89-7.77 (m, 2H), 7.71 (dd, J=6.7, 2.4 Hz, 1H), 7.55 (d, J=8.4 Hz, 1H), 7.43 (t, J=9.3 Hz, 1H), 6.94 (t, J=8.6 Hz, 1H), 3.07 (s, 3H), 2.55-2.65 (m, 1H), 2.58 (s, 3H), 1.35 (s, 3H), 0.80-1.00 (m, 2H), 0.55-0.80 (m, 2H).

Example 10 Preparation of Compound 10

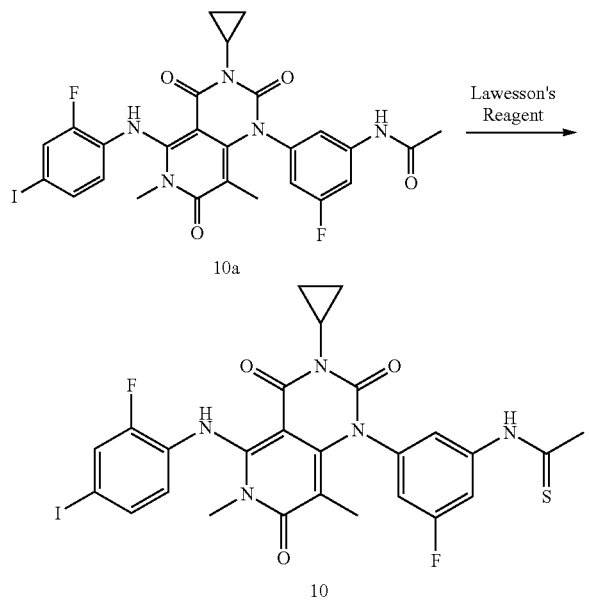

Compound 10a was synthesized as a starting material for the preparation of compound 10 by a method similar to examples 1 and 2.

Under a nitrogen atmosphere, a tetrahydrofuran solution (20 mL) of compound 10a (700 mg, 1.10 mmol) and Lawesson's reagent (875 mg, 2.20 mmol) was heated at 70° C. for 3 h. After the reaction was complete, the reaction mixture was concentrated and purified by silica gel column chromatography (eluent:petroleum ether/ethyl acetate=1-2:1) to give 589 mg of a light yellow solid as compound 10 (82% yield).

MS(ESI): m/z [M+H]$^+$: 649.8

$^1$H NMR (400 MHZ, DMSO-d$_6$, δ, ppm): 11.83 (s, 1H), 11.02 (s, 1H), 8.06 (d, J=10.7 Hz, 1H), 7.79 (d, J=10.2 Hz, 1H), 7.45-7.60 (m, 2H), 7.25 (d, J=9.2 Hz, 1H), 6.94 (t, J=8.6 Hz, 1H), 3.08 (s, 3H), 2.50-2.65 (m, 1H), 2.61 (s, 3H), 1.35 (s, 3H), 0.80-1.00 (m, 2H), 0.55-0.70 (m, 2H).

Example 11 Preparation of Compound 11

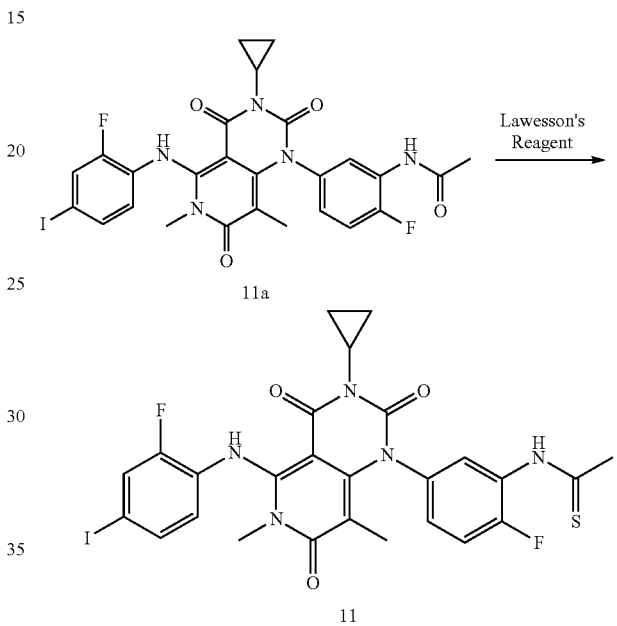

Compound 11a was synthesized as a starting material for the preparation of compound 11 by a method similar to examples 1 and 2.

Under a nitrogen atmosphere, a tetrahydrofuran solution (20 mL) of compound 11a (800 mg, 1.25 mmol) and Lawesson's reagent (1.0 g, 2.50 mmol) was heated at 70° C. for 3 hours. At the end of the reaction, the reaction mixture was concentrated and purified by silica gel column chromatography (eluent:petroleum ether/ethyl acetate=1-2:1) to give 665 mg of a pale yellow solid as compound 11 (82% yield).

MS(ESI): m/z [M+H]$^+$=650.0

$^1$H NMR (400 MHZ, DMSO-d$_6$, δ, ppm): 11.49 (s, 1H), 11.04 (s, 1H), 7.79 (dd, J=10.3, 1.8 Hz, 1H), 7.50-7.60 (m, 2H), 7.41 (d, J=8.0 Hz, 2H), 6.92 (t, J=8.7 Hz, 1H), 3.07 (s, 3H), 2.50-2.65(m, 1H), 2.60 (s, 3H), 1.34 (s, 3H), 0.86-1.00 (m, 2H), 0.60-0.75 (m, 2H).

Example 12 Preparation of Compound 12

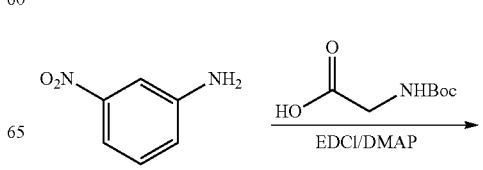

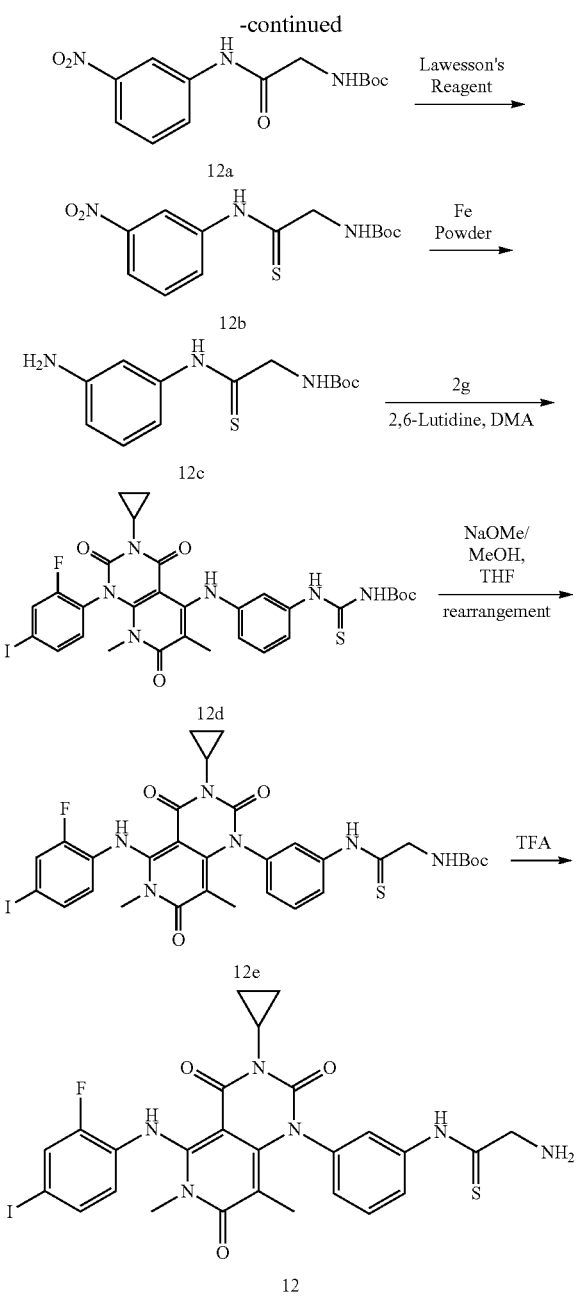

¹H-NMR (400 MHZ, CDCl₃, δ, ppm): 9.29 (s, 1H), 8.38 (s, 1H), 7.83 (dd, J=14.0, 8.2 Hz, 2H), 7.38 (t, J=8.2 Hz, 1H), 5.81 (s, 1H), 4.03 (d, J=5.5 Hz, 2H), 1.45 (s, 9H).

(2) Synthesis of Compound 12b

Under a nitrogen atmosphere, a mixture of compound 12a (5.9 g, 20.0 mmol), Lawesson's reagent (16.1 g, 40.0 mmol) and dried tetrahydrofuran (100 mL) was heated at 70° C. under reflux for 12 hours. At the end of the reaction, saturated aqueous sodium bicarbonate solution (100 mL) was added to quench the reaction. The mixture was extracted with ethyl acetate (50 mL×3). The organic phases were combined, washed with saturated NaCl solution, dried with anhydrous sodium sulfate, concentrated under reduced pressure and purified by silica gel column chromatography (eluent:petroleum ether/ethyl acetate=2:1) to give 4.27 g of a pale yellow oil as compound 12b (68.6% yield).

MS(ESI): m/z [M-Boc+H]⁺=312.1

¹H-NMR (400 MHZ, CDCl₃, δ, ppm): 10.71 (s, 1H), 8.77 (t, J=2.1 Hz, 1H), 8.09 (ddd, J=9.8, 2.0, 1.3 Hz, 2H), 7.54 (t, J=8.2 Hz, 1H), 5.65 (t, J=6.0 Hz, 1H), 4.32 (d, J=6.2 Hz, 2H), 1.48 (s, 9H).

(3) Synthesis of Compound 12c

A mixture of compound 12b (2.18 g, 7.0 mmol), iron powder (1.96 g, 35.0 mmol), aqueous saturated ammonium chloride solution (10 mL) and ethanol (50 mL) was stirred under reflux at 90° C. for 10 minutes under a nitrogen atmosphere. At the end of the reaction, the reaction mixture was filtered, and the filter cake was washed with an appropriate amount of dichloromethane. The filtrate was extracted with dichloromethane (50 mL×2). The organic phases were combined, washed with saturated NaCl solution, dried with anhydrous sodium sulfate, concentrated under reduced pressure and purified by silica gel column chromatography (eluent:petroleum ether/ethyl acetate=2:1) to give 1.62 g of a yellow oil as compound 12c (82.4% yield).

¹H-NMR (400 MHZ, CDCl₃, δ, ppm): 10.05 (s, 1H), 7.17 (s, 1H), 7.09 (t, J=8.0 Hz, 1H), 6.92 (dd, J=8.0, 0.9 Hz, 1H), 6.51 (dd, J=8.0, 0.9 Hz, 1H), 5.81 (d, J=5.6 Hz, 1H), 4.19 (d, J=6.0 Hz, 2H), 3.80 (s, 2H), 1.44 (s, 9H).

(4) Synthesis of Compounds 12d

A mixture of compound 12c (703 mg, 2.5 mmol), compound 2g (1.69 g, 2.75 mmol), 2,6-dimethylpyridine (804 mg, 7.5 mmol) and DMA (30 mL) was stirred under nitrogen atmosphere at 130° C. for 3 hours. At the end of the reaction, water (100 mL) was added and the reaction mixture was extracted with ethyl acetate (50 mL×3). The organic phases were combined, washed with saturated NaCl solution, dried with anhydrous sodium sulfate, concentrated under reduced pressure and purified by silica gel column chromatography (eluent:petroleum ether/ethyl acetate=2:1) to give 680 mg of a light yellow solid as compound 12d (36.5% yield).

MS(ESI): m/z m/z [M+H]⁺=747.1

¹H-NMR (400 MHZ, CDCl₃, δ, ppm): 10.24 (s, 1H), 10.19 (s, 1H), 7.70-7.57 (m, 2H), 7.52 (s, 1H), 7.29 (d, J=7.2 Hz, 2H), 6.95 (t, J=7.9 Hz, 1H), 6.80 (d, J=7.0 Hz, 1H), 5.52 (s, 1H), 4.25 (d, J=6.2 Hz, 2H), 2.94 (s, 3H), 2.80-2.70 (m, 1H), 1.68 (s, 3H), 1.46 (s, 9H), 1.15 (d, J=7.3 Hz, 2H), 0.81 (dd, J=8.0, 3.4 Hz, 2H).

(5) Synthesis of Compound 12e

Under a nitrogen atmosphere, a methanol solution of sodium methoxide (30%, 1.5 mL) was added to a tetrahydrofuran solution (5 mL) of compound 12d (597 mg, 0.8 mmol). The reaction mixture was stirred for 0.5 hours at room temperature. At the end of the reaction, water (15 mL) was added and then the mixture was extracted with ethyl acetate (20 mL×3). The organic phases were combined, washed with saturated NaCl solution, dried with anhydrous (1) Synthesis of Compound 12a Under a nitrogen atmosphere, m-nitroaniline (3.45 g, 25.0 mmol), Boc-glycine (5.25 g, 30.0 mmol), 1-ethyl-3-(3-dimethylaminopropyl)carbodiimide (EDCI, 9.6 g, 50.0 mmol) and 4-dimethylaminopyridine (DMAP, 1.5 g, 12.5 mmol) were dissolved in dry dichloromethane (100 mL), and stirred at room temperature for 1 hour. At the end of the reaction, an aqueous saturated sodium bicarbonate solution (100 mL) was added to quench the reaction. The reaction mixture was extracted with dichloromethane (50 mL×2). The organic phases were combined, washed with saturated NaCl solution, dried with anhydrous sodium sulfate, concentrated under reduced pressure and purified by silica gel column chromatography (eluent:petroleum ether/ethyl acetate=3:1) to give 6.85 g of a yellow oil as compound 12a (92.8% yield).

sodium sulfate, concentrated under reduced pressure and purified by silica gel column chromatography (eluent:petroleum ether/ethyl acetate=3:1) to give 413 mg of a yellow solid as compound 12e (69.2% yield).

MS(ESI): m/z [M+H]$^+$=747.1

$^1$H-NMR (400 MHZ, CDCl$_3$, δ, ppm): 11.26 (s, 1H), 10.33 (s, 1H), 8.02 (s, 1H), 7.60-7.48 (m, 2H), 7.44 (d, J=8.5 Hz, 1H), 7.40 (t, J=8.1 Hz, 1H), 7.14 (d, J=8.1 Hz, 1H), 6.69 (t, J=8.3 Hz, 1H), 5.58 (s, 1H), 4.21 (d, J=6.1 Hz, 2H), 3.19 (s, 3H), 2.78-2.68 (m, 1H), 1.46 (s, 9H), 1.43 (s, 3H), 1.11 (q, J=6.6 Hz, 2H), 0.78 (q, J=7.1 Hz, 2H).

(6) Synthesis of Compound 12

Compound 12e (400 mg, 0.536 mmol) was dissolved in dichloromethane (20 mL) and then trifluoroacetic acid (7 mL) was slowly added at 0° C. The reaction mixture was stirred for 3 hours at room temperature. At the end of the reaction, the reaction mixture was concentrated. The residue was dissolved in ethyl acetate (20 mL) and washed with saturated aqueous sodium bicarbonate solution (20 mL). The aqueous phase was extracted with ethyl acetate (10 mL×2). The organic phases were combined, dried with anhydrous sodium sulfate, concentrated under reduced pressure, and purified by silica gel column chromatography (eluent:dichloromethane/methanol=60:1) to give 260 mg of a light yellow solid as compound 12 (75% yield).

MS(+ESI): m/z [M+1]$^+$=647.1

$^1$H NMR (400 MHZ, DMSO-d$_6$, δ, ppm): 11.27 (s, 1H), 8.05 (t, J=2.0 Hz, 1H), 7.96 (dd, J=8.1, 1.2 Hz, 1H), 7.51 (dd, J=9.7, 1.8 Hz, 1H), 7.46 (t, J=8.1 Hz, 2H), 7.17 (dd, J=8.0, 1.2 Hz, 1H), 6.69 (t, J=8.3 Hz, 1H), 3.88 (s, 2H), 3.19 (s, 3H), 2.66-2.76 (m, 1H), 1.45 (s, 3H), 1.06-1.16 (m, 2H), 0.75-0.85 (m, 2H).

Example 13 Preparation of Compound 13

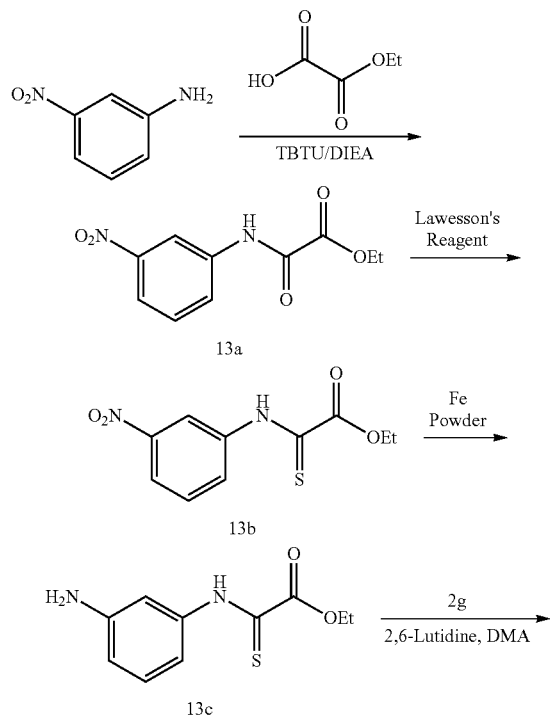

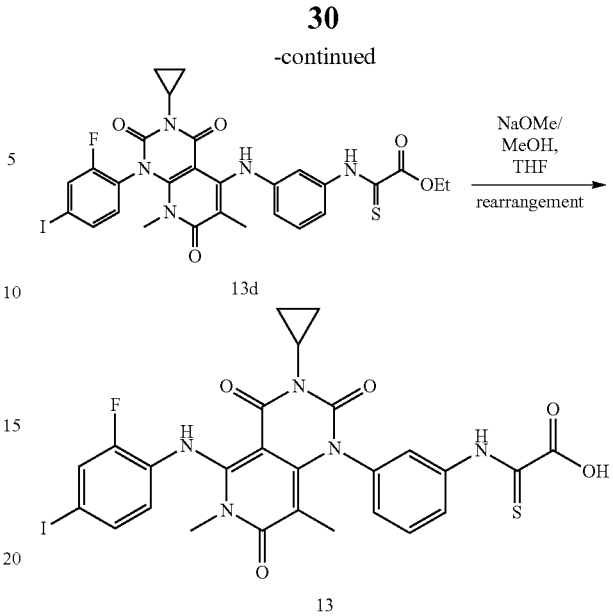

(1) Synthesis of Compound 13a

Under a nitrogen atmosphere, m-nitroaniline (1.4 g, 10.1 mmol), oxalic acid monoethyl ester (1.8 g, 15.2 mmol), 2-(1H-benzotriazole-1-yl)-1,1,3,3-tetramethylaminium tetrafluoroborate (TBTU, 6.5 g, 20.2 mmol) and N,N-diisopropylethylamine (DIEA, 3.1 g, 24.4 mmol) were dissolved in dry dichloromethane (25 mL), and the mixture was stirred at room temperature for 5 hours. At the end of the reaction, water (25 mL) was added to the reaction mixture and then the mixture was extracted with dichloromethane (25 mL×3). The organic phases were combined, washed successively with 10% aqueous citric acid solution (25 mL), saturated aqueous sodium bicarbonate solution (25 mL) and saturated NaCl solution (25 mL), dried with anhydrous sodium sulfate, concentrated under reduced pressure and purified by silica gel column chromatography (eluent: petroleum ether/ethyl acetate=10:1) to give 2.01 g of a light yellow solid as compound 13a (83.6% yield).

MS(ESI): m/z [M+H]$^+$=239.1

$^1$H-NMR (400 MHZ, CDCl$_3$, δ, ppm): 9.17 (s, 1H), 8.51 (t, J=2.1 Hz, 1H), 8.15-8.00 (m, 2H), 7.57 (t, J=8.2 Hz, 1H), 4.44 (q, J=7.1 Hz, 2H), 1.44 (t, J=7.1 Hz, 3H).

(2) Synthesis of Compound 13b

A mixture of compound 13a (1.4 g, 6.3 mmol), Lawesson's reagent (7.6 g, 18.9 mmol) and anhydrous tetrahydrofuran (40 mL) was stirred under a nitrogen atmosphere at 70° C. for 12 hours. The reaction was quenched with saturated aqueous sodium bicarbonate solution (40 mL) and the mixture was extracted with ethyl acetate (45 mL×3). The organic phases were combined, washed with saturated NaCl solution (100 mL), dried with anhydrous sodium sulfate, concentrated under reduced pressure and purified by silica gel column chromatography (eluent:petroleum ether/ethyl acetate=10:1) to give 1.15 g of a red solid as compound 13b (71.9% yield).

MS(ESI): m/z [M+H]$^+$=255.04

$^1$H-NMR (400 MHZ, CDCl$_3$, δ, ppm): 10.74 (s, 1H), 8.99 (t, J=2.2 Hz, 1H), 8.28 (ddd, J=8.1, 2.1, 0.6 Hz, 1H), 8.15 (ddd, J=8.3, 2.2, 0.9 Hz, 1H), 7.65-7.57 (m, 1H), 4.44 (q, J=7.1 Hz, 2H), 1.44 (t, J=7.1 Hz, 3H).

(3) Synthesis of Compound 13c

Under a nitrogen atmosphere, a mixture of compound 13b (850 mg, 3.3 mmol), iron powder (1.1 g, 19.8 mmol), aqueous saturated ammonium chloride solution (2 mL), and ethanol (20 mL) was stirred at 90° C. under reflux for 1 hour. At the end of the reaction, the reaction mixture was filtered, and the filtrate was concentrated under reduced pressure and purified by silica gel column chromatography (eluent:petroleum ether/ethyl acetate=8:1) to give 490 mg of a yellow solid as compound 13c (66.4% yield).

MS(ESI): m/z [M+H]$^+$=225.0

$^1$H-NMR (400 MHz, CDCl$_3$, δ, ppm): 10.51 (s, 1H), 7.66 (t, J=2.1 Hz, 1H), 7.26-7.00 (m, 2H), 6.61 (ddd, J=7.9, 2.2, 0.9 Hz, 1H), 4.42 (q, J=7.1 Hz, 2H), 3.81 (s, 2H), 1.44 (t, J=7.1 Hz, 3H).

(4) Synthesis of Compound 13d

A mixture of compound 13c (200 mg, 0.91 mmol), compound 2g (615 mg, 1.0 mmol), 2,6-dimethylpyridine (205 mg, 1.91 mmol) and DMA (5 mL) was stirred at 100° C. for 10 hours under a nitrogen atmosphere. After completion of the reaction, water (50 mL) was added into the reaction mixture, and then the reaction mixture was extracted with dichloromethane (50 mL×3). The organic phases were combined, washed successively with 10% aqueous citric acid solution (100 mL), saturated aqueous sodium bicarbonate solution (100 mL) and saturated NaCl solution (100 mL) in sequence, dried with anhydrous sodium sulfate, concentrated under reduced pressure and purified by silica gel column chromatography (eluent:petroleum ether/ethyl acetate=10:1) to give 363 mg of a light yellow solid as compound 13d (57.9% yield).

MS(ESI): m/z [M+H]$^+$=690.1

$^1$H-NMR (400 MHZ, CDCl$_3$, δ, ppm): 10.52 (s, 1H), 10.21 (s, 1H), 7.70 (t, J=2.0 Hz, 1H), 7.68-7.60 (m, 2H), 7.56 (dd, J=7.9, 1.7 Hz, 1H), 7.34 (t, J=8.1 Hz, 1H), 6.99-6.92 (m, 1H), 6.85 (dd, J=8.0, 2.0 Hz, 1H), 4.43 (q, J=7.1 Hz, 2H), 2.96 (s, 3H), 2.80-2.73 (m, 1H), 1.70 (s, 3H), 1.59 (s, 3H), 0.99-0.75 (m, 4H).

(5) Synthesis of Compound 13

Under a nitrogen atmosphere, compound 13d (100 mg, 0.15 mmol) was dissolved in tetrahydrofuran (20 mL), and a methanol solution of sodium methoxide (28%, 0.5 mL) was added. The reaction mixture was stirred for 0.5 hours at room temperature. At the end of the reaction, water (30 mL) was added and the reaction mixture was extracted with dichloromethane (30 mL×3). The organic phases were combined, washed successively with 10% aqueous citric acid solution (50 mL), saturated aqueous sodium bicarbonate solution (50 mL) and saturated NaCl solution (50 mL), dried with anhydrous sodium sulfate, concentrated under reduced pressure and purified by silica gel column chromatography (eluent:dichloromethane/methanol/acetic acid=250/10/1) to give 23 mg of a yellow solid as compound 13 (23.2% yield).

MS(ESI): m/z [M+H]$^+$=662.0

$^1$H-NMR (400 MHZ, CDCl$_3$, δ, ppm): 11.28 (s, 1H), 10.87 (s, 1H), 8.14-7.89 (m, 2H), 7.49 (dd, J=23.0, 8.5 Hz, 3H), 7.27 (s, 1H), 6.71 (t, J=8.3 Hz, 1H), 3.20 (s, 3H), 2.81-2.71 (m, 1H), 1.42 (s, 3H), 1.02-0.67 (m, 4H).

Example 14 Inhibitory Activity of Compounds on Dual Specificity Mitogen-Activated Protein Kinase 1 (MEK) and Dual Specificity Mitogen-Activated Protein Kinase 2 (MEK2)

Experimental purpose: The inhibitory activity of the compounds on MEK1 and MEK2 was measured by performing a Raf-MEK-ERK cascade kinase assay using recombinant protein.

Experimental method: 2 mg of dephosphorylated myelin basic protein (MBP) was dispersed in a 0.2 M sodium carbonate aqueous solution (pH=9.4). The mixed solution was then coated onto an enzyme-linked immunosorbent assay (ELISA) plate (U-shaped bottom plate) and left to stand overnight at 4° C. A mixed solution with an initial concentration of 3.0 μM was serially diluted 3-fold with dimethyl sulfoxide (DMSO) to give a total of 10 concentrations: 3.0 μM, 1.0 μM, 0.33 μM, 0.11 μM, 0.037 μM, 0.012 μM, 0.0041 μM, 0.0014 μM, 0.00045 μM and 0.00015 μM. Compound solutions with serial concentrations were tested in triplicate wells. A mixture of 2 ng of inactivated MEK1 (or 4 ng of MEK2) and 50 ng of inactivated ERK2 was dissolved in a buffer solution (20 mM MOPS [pH=7.4], 0.1% 2-mercaptoethanol, 0.1% BSA) at room temperature, and then treated with the above serial solutions on a flat plate. The plate was covered with 1% bovine serum albumin (BSA) and pre-incubated for 10 minutes. Active B-Raf (V599E) (containing 10 μM adenosine triphosphate (ATP) and 12.5 mM MgCl$_2$) was added to initiate the kinase reaction. After incubation at 30° C. for 30 minutes, phosphorylation of MBP by ERK was detected using peroxidase-labeled anti-phosphorylated MBP antibodies. Data curves were plotted and half maximal inhibitory concentration (IC$_{50}$) values were calculated using XLFit. The results are presented in Table 1.

TABLE 1

| | IC$_{50}$ of compounds for the MEK1/MEK2 | |
|---|---|---|
| Compound | MEK1 IC$_{50}$(nM) | MEK2 |
| 1 | 1.21 | 1.09 |
| 2 | 1.83 | 2.13 |
| 3 | 0.90 | 0.98 |
| 4 | 1.36 | 1.05 |
| 5 | 0.99 | 1.19 |
| 6 | 1.88 | 1.24 |
| 7 | 0.95 | 1.01 |
| 8 | 1.57 | 2.08 |
| 9 | 2.29 | 2.26 |
| 10 | 2.01 | 2.07 |
| 11 | 1.37 | 1.54 |
| 12 | 1.51 | 2.13 |
| 13 | 2.38 | 2.64 |
| Trametinib | 5.28 | 4.84 |

The results indicated that compounds 1 to 13 exhibited higher activity as MEK1/2 inhibitors compared to Trametinib (more than twice that of Trametinib).

Example 15 Anti-Proliferative Activity of Compounds on Cancer Cells

Experimental purpose: The anti-proliferative activity of compounds 1 to 13 and Trametinib on human malignant melanoma cells (A375), human colon cancer cells (HCT-15 and HCT116), human non-small cell lung cancer cells (A549), and human prostate cancer cells (PC-3) was evaluated using a Cell Counting Kit-8 (CCK-8) assay.

Experimental procedure: Sample solutions with a concentration of 20 μM were prepared and serially diluted 5-fold downwards to obtain 10 concentrations: 20000 nM, 4000 nM, 800 nM, 160 nM, 32 nM, 6.4 nM, 1.28 nM, 0.256 nM, 0.0512 nM and 0.01024 nM. The sample solutions were incubated with the above cell lines for 72 h. Then 10 μL of a CCK-8 solution was then added to each well, followed by a further 2 hours incubation. An optical density (OD) value was measured at 450 nm using a fully automated microplate reader. Data were processed using GraphPad Prism 7 to calculate IC$_{50}$. The results of the experiments are presented in Table 2.

TABLE 2

| Compound | A375 | HCT-15 | A549 $IC_{50}(\mu M)$ | HCT116 | PC-3 |
|---|---|---|---|---|---|
| 1 | 0.0035 | 0.0154 | 0.0026 | 0.0029 | 0.0024 |
| 2 | 0.0031 | 0.0126 | 0.0031 | 0.0026 | 0.0036 |
| 3 | 0.0025 | 0.0148 | 0.0015 | 0.0021 | 0.0019 |
| 4 | 0.0039 | 0.0098 | 0.0024 | 0.0016 | 0.0014 |
| 5 | 0.0026 | 0.0201 | 0.0036 | 0.0038 | 0.0033 |
| 6 | 0.0029 | 0.0139 | 0.0039 | 0.0016 | 0.0028 |
| 7 | 0.0043 | 0.0242 | 0.0028 | 0.0027 | 0.0021 |
| 8 | 0.0047 | 0.0258 | 0.0058 | 0.0042 | 0.0024 |
| 9 | 0.0028 | 0.0216 | 0.0044 | 0.0052 | 0.0019 |
| 10 | 0.0018 | 0.0149 | 0.0085 | 0.0064 | 0.0023 |
| 11 | 0.0024 | 0.0218 | 0.0034 | 0.0031 | 0.0027 |
| 12 | 0.0031 | 0.0227 | 0.0031 | 0.0036 | 0.0023 |
| 13 | 0.0042 | 0.0317 | 0.0064 | 0.0052 | 0.0045 |
| Trametinib | 0.0125 | 0.0983 | 0.0332 | 0.0327 | 0.0126 |

$IC_{50}$ of compounds for various cancer cells

The results showed that for all five cancer cells tested, compounds 1 to 13 had higher in vitro cancer cell proliferation inhibitory activity than the reference compound, Trametinib.

Example 16 In Vivo Anti-Tumor Assay

Experimental purpose: To evaluate the in vivo efficacy of the compounds in a subcutaneous xenograft model of human cancer cells in a Bagg's albino (BALB/c) nude mouse.

Experimental procedure: The study evaluated the inhibitory effect of compounds administered by gavage against human HCT116 subcutaneous xenograft tumors in the BALB/c nude mouse model by measuring tumor size and calculating tumor volume (TV), relative tumor volume (RTV), relative tumor proliferation rate (T/C), and anti-tumor efficacy (TGI). The experimental groupings and dosing regimens are shown in Table 3.

TABLE 3

Grouping and dosing regimen

| Group | Number of animals | Compound | Dose (mg/kg) | Route of administration | Frequency |
|---|---|---|---|---|---|
| 1 | 10 | Solvent control group | — | Oral administration (P.O.) | Quaque die (QD) × 30 days |
| 2 | 10 | Trametinib | 3 | P.O. | QD × 30 days |
| 3 | 10 | Compound 2 | 3 | P.O. | QD × 30 days |
| 4 | 10 | Compound 8 | 3 | P.O. | QD × 30 days |
| 5 | 10 | Compound 12 | 3 | P.O. | QD × 30 days |

The changes in body weight of mice after 30 days of continuous gavage of the compound at a dose of 3 mg/kg are shown in FIG. 1.

FIG. 1 shows that the weight loss in the Trametinib group (group 2) at the end of the experiment was significantly higher than that in groups 3, 4 and 5, indicating that the toxicity of Trametinib was higher than that of compounds 2, 8 and 12.

Figure 2:
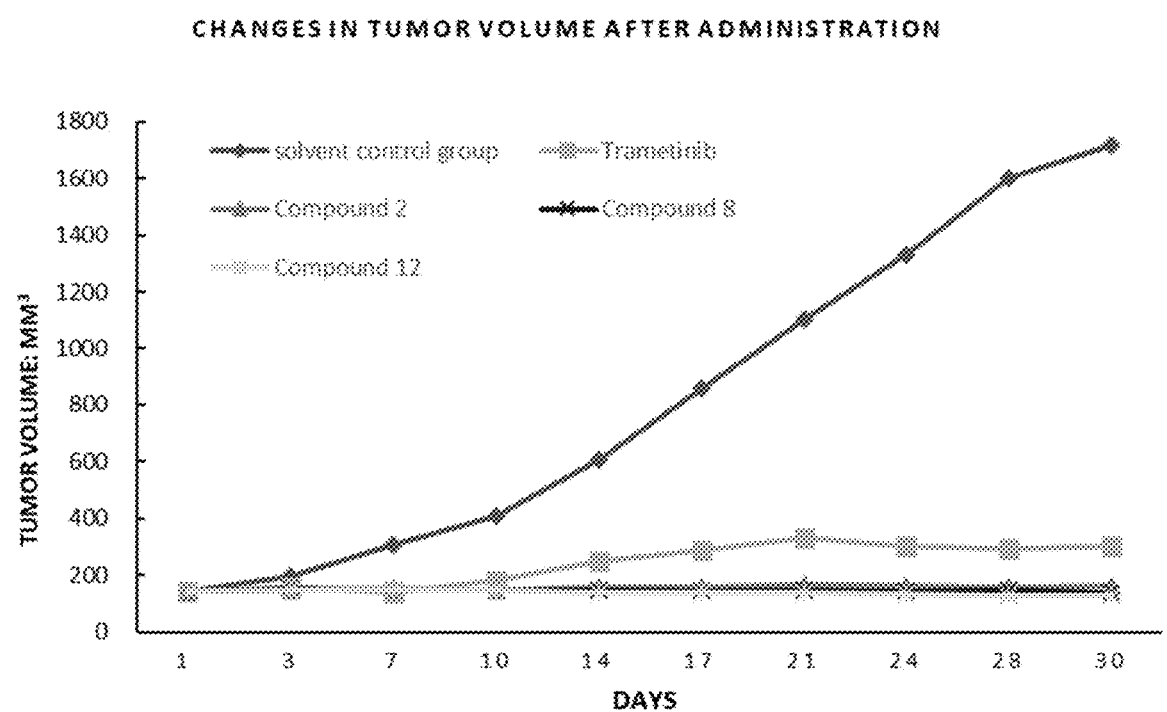
FIG. 2 shows a curve of tumor volume change in the experimental mice described in Example 16 of the present disclosure.

The changes in tumor volume in mice are shown in FIG. 2.

FIG. 2 shows that the tumor growth was effectively inhibited in all groups. However, compared to the Trametinib group, compounds 2, 8 and 12 had better inhibitory effects.

The tumor suppressive efficacy of the compounds was quantified by TGI (%) or relative tumor proliferation rate T/C (%). TGI (%) reflected the tumor growth inhibition rate.

TGI(%) was calculated using the following equation: TGI(%)=[1−(mean tumor volume at the end of treatment in a treatment group−mean tumor volume at the start of treatment in the treatment group)/(mean tumor volume at the end of treatment in the solvent control group−mean tumor volume at the start of treatment in the solvent control group)]×100%.

T/C(%) was calculated using the following equation: T/C(%)=TRTV/CRTV×100%, where TRTV was an RTV of the treatment group, and CRTV was an RTV of the negative control group. The RTV was calculated from the results of tumor size measurements according to the following equation: RTV=Vt/V0, where V0 was a mean tumor volume measured on the day of first administration (i.e., day 0), Vt was a mean tumor volume measured on the day indicated, and TRTV and CRTV were obtained from data on the same day.

A p-value was calculated based on tumor volume, indicating the probability that the observed results occurred by chance.

The evaluation of the tumor suppressive efficacy of Trametinib and compounds 2, 8 and 12 in the xenograft tumor model is shown in Table 4.

TABLE 4

| Evaluation of tumor suppressive efficacy | | | | |
| --- | --- | --- | --- | --- |
| Group | Tumor volume (mm$^3$) (Day 30) | T/C (%) | TGI (%) | p |
| Solvent control group | 1714 ± 227 | — | — | — |
| Trametinib | 305 ± 34 | 17.79 | 89.80 | 0.001 |
| Compound 2 | 165 ± 21 | 9.62 | 98.72 | <0.001 |
| Compound 8 | 140 ± 26 | 8.17 | 100.32 | <0.001 |
| Compound 12 | 128 ± 19 | 7.47 | 101.08 | <0.001 |

The above embodiments are merely illustrative, and are not intended to limit the present disclosure. It should be noted that various modifications and improvements made by those of ordinary skill in the art without departing from the spirit of the present disclosure shall fall within the scope of the present disclosure defined by the appended claims.

What is claimed is:

1. A thioamide derivative, wherein the thioamide derivative is selected from the group consisting of:

1

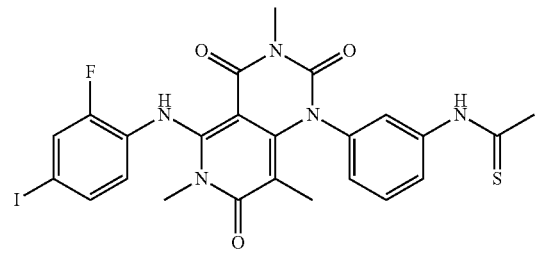

2

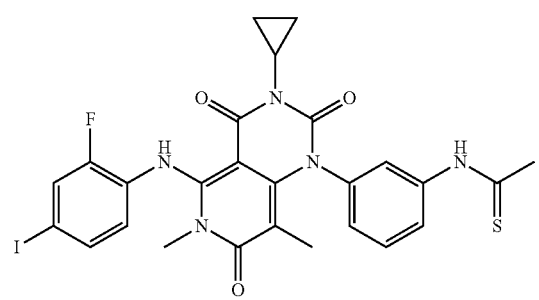

3

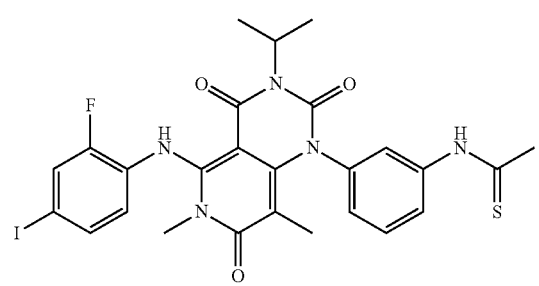

-continued

4

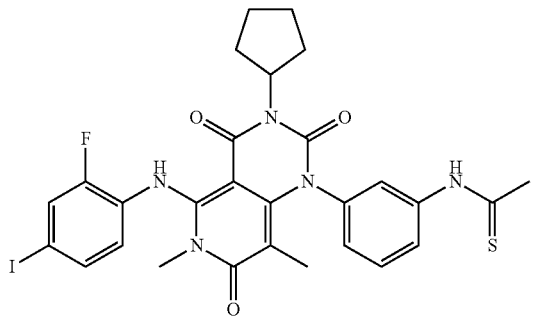

5

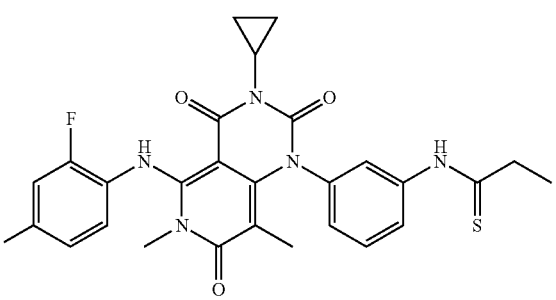

6

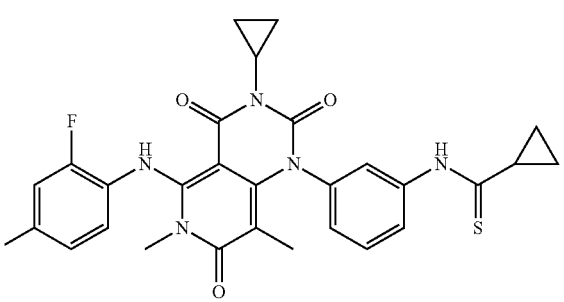

7

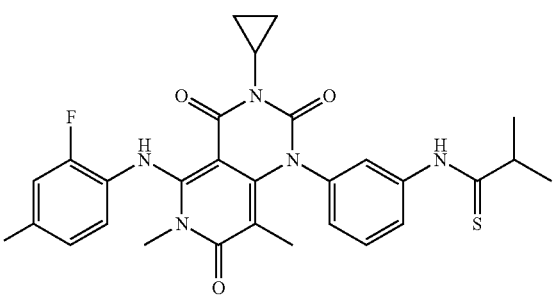

8

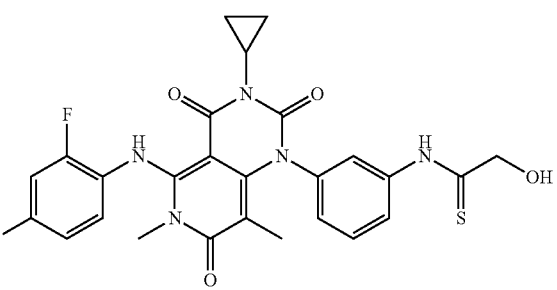

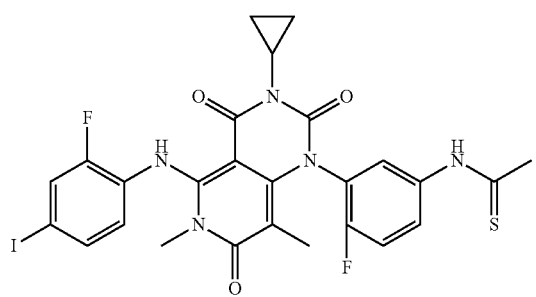

9

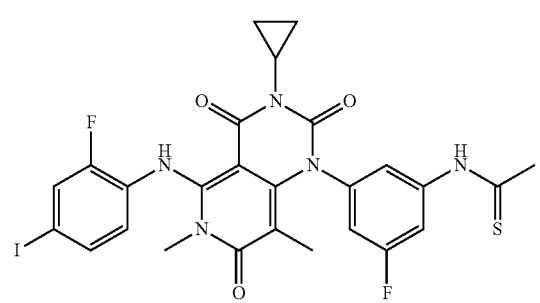

10

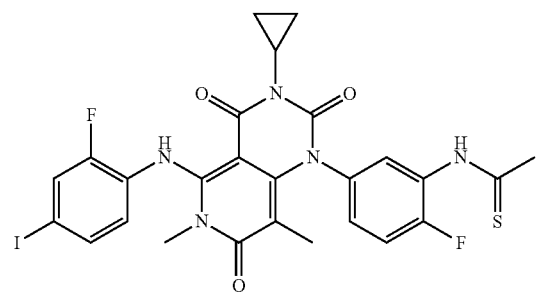

11

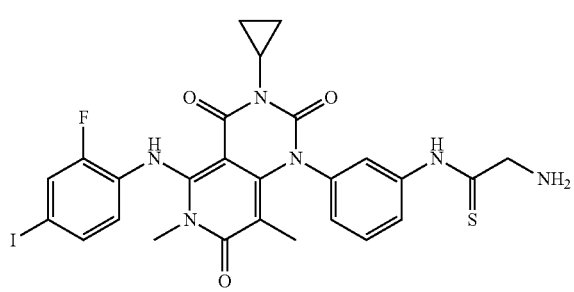

12

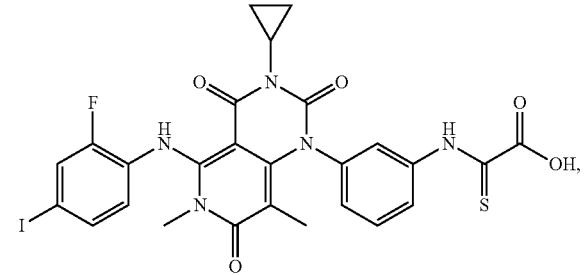

13 and a pharmaceutically-acceptable salt thereof.

2. A pharmaceutical composition, comprising:
   a therapeutically effective amount of the thioamide derivative of claim 1 or a pharmaceutically-acceptable salt thereof.

3. The pharmaceutical composition of claim 2, further comprising:
   one or more pharmaceutically-acceptable carriers, diluents or excipients.

4. A method for treating a cancer in a patient in need thereof, comprising:
   administering a therapeutically effective amount of the thioamide derivative of claim 1 or a pharmaceutically-acceptable salt thereof to the patient;
   wherein the cancer is selected from the group consisting of malignant melanoma, colon cancer, non-small cell lung cancer and prostate cancer.

5. A method for treating a cancer in a patient in need thereof, comprising:
   administering a therapeutically effective amount of the pharmaceutical composition of claim 2 to the patient;
   wherein the cancer is selected from the group consisting of malignant melanoma, colon cancer, non-small cell lung cancer and prostate cancer.

6. A method for treating a cancer in a patient in need thereof, comprising:
   administering a therapeutically effective amount of the thioamide derivative of claim 1 or a pharmaceutically-acceptable salt thereof to the patient in combination with an anticancer agent;
   wherein the cancer is selected from the group consisting of malignant melanoma, colon cancer, non-small cell lung cancer and prostate cancer.

7. The method of claim 6, wherein the anticancer agent is selected from the group consisting of adriamycin, bleomycin, vinblastine, taxane, etoposide, 5-fluorouracil, cyclophosphamide, methotrexate, cisplatin, retinoic acid, temozolomide, dactinomycin, imatinib, gefitinib, sorafenib, erlotinib, sunitinib, afatinib, cabozantinib, osimertinib, rituximab, cetuximab, trastuzumab, nivolumab, pembrolizumab, atezolizumab, durvalumab, avelumab and a combination thereof.

\* \* \* \* \*